(12) United States Patent
Allbritton et al.

(10) Patent No.: US 11,193,110 B2
(45) Date of Patent: Dec. 7, 2021

(54) METHODS TO GENERATE GASTROINTESTINAL EPITHELIAL TISSUE CONSTRUCTS

(71) Applicant: The University of North Carolina at Chapel Hill, Chapel Hill, NC (US)

(72) Inventors: Nancy Allbritton, Chapel Hill, NC (US); Yuli Wang, Cary, NC (US); Christopher Sims, Chapel Hill, NC (US); Scott Magness, Chapel Hill, NC (US); Scott Bultman, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/545,456

(22) PCT Filed: Jan. 29, 2016

(86) PCT No.: PCT/US2016/015631
§ 371 (c)(1),
(2) Date: Jul. 21, 2017

(87) PCT Pub. No.: WO2016/123474
PCT Pub. Date: Aug. 4, 2016

(65) Prior Publication Data
US 2018/0002672 A1    Jan. 4, 2018

Related U.S. Application Data

(60) Provisional application No. 62/110,147, filed on Jan. 30, 2015.

(51) Int. Cl.
*C12N 5/071* (2010.01)
*C12Q 1/08* (2006.01)

(52) U.S. Cl.
CPC ......... *C12N 5/0697* (2013.01); *C12N 5/0679* (2013.01); *C12Q 1/08* (2013.01);
(Continued)

(58) Field of Classification Search
CPC ................ C12N 5/0679; C12N 5/0697; C12N 2533/54; C12N 2501/15; C12N 2501/727;
(Continued)

(56) References Cited

U.S. PATENT DOCUMENTS 8,946,305 B2    2/2015  Liao et al.
9,040,665 B2    5/2015  Wnek et al.
(Continued)

FOREIGN PATENT DOCUMENTS

EP          3491122        6/2019
JP          2008513159 A   5/2008
(Continued)

OTHER PUBLICATIONS

Tang et al. Utilization of a Human Intestinal Epithelial Cell Culture System (Caco-2) for Evaluating Cytoprotective Agents. Pharm Res (1993), v10(11), p. 1620-1626. (Year: 1993).*
(Continued)

*Primary Examiner* — Sean C. Barron
(74) *Attorney, Agent, or Firm* — Jenkins, Wilson, Taylor & Hunt, P.A.

(57) ABSTRACT

A method of making a live cell construct is carried out by: (a) providing a non-cellular support having a top surface and a bottom surface, (b) contacting live undifferentiated cells to the non-cellular support, and then (c) propagating a gastrointestinal epithelial cell monolayer on said top surface. In some embodiments, the live cells in the monolayer include: (i) undifferentiated cells (e.g., stem or progenitor cells); and (ii) optionally, but in some embodiments preferably, differentiated cells (e.g., enterocytes, Paneth cells, enteroendo-
(Continued)

crine cells, tuft cells, microcells, intra-epithelial lymphocytes, and/or goblet cells). Constructs formed by such methods and methods of using the same (e.g., in high through-put screening) are also described.

24 Claims, 11 Drawing Sheets

(52) U.S. Cl.
CPC ...... C12N 2501/11 (2013.01); C12N 2501/15 (2013.01); C12N 2501/415 (2013.01); C12N 2501/727 (2013.01); C12N 2501/998 (2013.01); C12N 2501/999 (2013.01); C12N 2513/00 (2013.01); C12N 2533/54 (2013.01); C12N 2533/90 (2013.01); C12N 2535/00 (2013.01); C12N 2537/10 (2013.01); G01N 2500/10 (2013.01)

(58) Field of Classification Search
CPC ........ C12N 2501/998; C12N 2501/999; C12N 2533/90; C12N 2535/00; C12N 2537/10; C12N 2501/11; C12N 2501/415; C12N 2513/00; C12Q 1/08; G01N 2500/10
See application file for complete search history.

(56) References Cited

U.S. PATENT DOCUMENTS

| | | |
|---|---|---|
| 9,132,208 B2 | 9/2015 | Chen et al. |
| 9,200,676 B2 | 12/2015 | Yamaguchi |
| 9,205,172 B2 | 12/2015 | Neethling et al. |
| 9,211,362 B2 | 12/2015 | Hwang et al. |
| 9,272,004 B2 | 3/2016 | Nataraj et al. |
| 9,283,301 B1 | 3/2016 | Simionescu et al. |
| 2003/0017142 A1 | 1/2003 | Toner et al. |
| 2005/0106717 A1 | 5/2005 | Wilson et al. |
| 2006/0019389 A1 | 1/2006 | Yayon et al. |
| 2006/0121609 A1 | 6/2006 | Yannas et al. |
| 2007/0134790 A1 | 1/2007 | Gould et al. |
| 2012/0089238 A1 | 4/2012 | Kang et al. |
| 2014/0093478 A1 | 4/2014 | Turnbaugh et al. |
| 2017/0306278 A1 | 10/2017 | Nguyen et al. |
| 2019/0211296 A1 | 7/2019 | Allbritton |
| 2021/0087515 A1 | 3/2021 | Allbritton et al. |

FOREIGN PATENT DOCUMENTS

| | | |
|---|---|---|
| JP | 2011523355 A | 8/2011 |
| JP | 2012500371 | 1/2012 |
| JP | 2014514942 A | 6/2014 |
| WO | WO 2005/072419 | 8/2005 |
| WO | WO 2009/132196 | 10/2009 |
| WO | WO/2009/132196 | 10/2009 |
| WO | WO/2012/136701 | 10/2012 |
| WO | WO 2014/186430 | 11/2014 |
| WO | WO/2018/022548 | 2/2018 |
| WO | WO/2018/022548 A1 | 2/2018 |
| WO | WO 2019/141824 A1 | 7/2019 |
| WO | WO 2019/222333 | 11/2019 |
| WO | WO 2019/227012 | 11/2019 |
| WO | WO2020102682 | 5/2020 |

OTHER PUBLICATIONS

Ferruzza et al. A protocol for differentiation of human intestinal Caco-2 cells in asymmetricserum-containing medium. Toxicology in Vitro (2012), v26, p. 1252-1255. (Year: 2012).*
Wang et al. Influence of micro-well biomimetic topography on intestinal epithelial Caco-2 cell phenotype. Biomaterials (2009), v30, p. 6825-6834. (Year: 2009).*
Bishop et al. Regulation of Caco-2 cell proliferation by basolateral membrane epidermal growth factor receptors. Am J. Physiol (1994), v267(5 Pt. 1), G892-900. (Year: 1994).*
Transwell® permeable supports (2007), 8 pages. (Year: 2007).*
Deveney et al. Establishment of Human Colonic Epithelial Cells in Long-Term Culture. Journal of Surgical Research (1996), 64, 161-169. (Year: 1996).*
Hass et al. Lack of Butyrate is Associated With Induction of Bax and Subsequent Apoptosis in the Proximal Colon of Guinea Pig. Gastroenterology (1997), 112:875-881. (Year: 1997).*
Strater et al. Rapid Onset of Apoptosis In Vitro Follows Disruption of beta1-Integrin/Matrix Interactions in Human Colonic Crypt Cells . Gastroenterology (1996), 110, 1776-1784. (Year: 1996).*
Ramanujan et al. Diffusion and Convection in Collagen Gels: Implications for Transport in the Tumor Interstitium. Biophysical Journal (2002), 83, 1650-1660. (Year: 2002).*
Jung et al. Isolation and in vitro expansion of human colonic stem cells. Nature Medicine (2011), 17(10), 1225-1227. (Year: 2011).*
Cell Culture Inserts, 0.4um, Falcon®. MG Scientific, internet article (2014). (Year: 2014).*
Maenosono et al. A Transparent Polyimide Film as a Biological Cell Culture heet with Microstructures. Journal of Biomaterials and Nanobiotechnology, 2014, 5, 17-23. (Year: 2014).*
Gracz et al. Identification, Isolation, and Culture of Intestinal Epithelial Stem Cells from Murine Intestine. Methods Mol Biol. 2012 ; 879, 23 page author manuscript. (Year: 2012).*
Sträter et al. Rapid Onset of Apoptosis In Vitro Follows Disruption of beta1-Integrin/Matrix Interactions in Human Colonic Crypt Cells . Gastroenterology (1996), 110, 1776-1784. (Year: 1996).*
Frantz et al. The extracellular matrix at a glance. Journal of Cell Science (2010), 123, 4195-4200. (Year: 2010).*
Munoz-Pinto et al. Lamina Propria Cellularity and Collagen Composition: An Integrated Assessment of Structure in Humans. Annals of Otology, Rhinology, and Laryngology (2009), 118(4), 299-306. (Year: 2009).*
Petersen et al. Generation of L Cells in Mouse and Human Small Intestine Organoids. Diabetes (epub Oct. 15, 2013), 63(2), 410-420. (Year: 2013).*
Alipour et al. Measurement of Vocal Folds Elastic Properties for Continuum Modeling. Journal of Voice (2012), 26(6), 816.e21-816.e29. (Year: 2012).*
Whitehead et al. A Method for the Isolation and Culture of Human Colonic Crypts in Collagen Gels. In Vitro Cellular and Developmental Biology (1987), 23(6), 436-442. (Year: 1987).*
Bartsch et al. Establishment of a Long-Term Culture System for Rat Colon Epithelial Cells. In Vitro Cell. Dev. Biol.-Animal (2004), 40, 278-284, (Year: 2004).*
Quaroni et al. Epithelioid Cell Cultures From Rat Small Intestine. J. Cell Biology (1979), 80, 248-265. (Year: 1979).*
Gibson et al. Isolation of Colonic Crypts That Maintain Structural and Metabolic Viability.In Vitro. Gastroenterology (1989), 96, 283-291. (Year: 1989).*
Watson, Carey et al. "An in vivo model of human small intestine using pluripotent stem cells", Nature Medicine, 20(11):1310-1314 (2014).
Spence, Jason et al. "Directed differentiation of human pluripotent stem cells into intestinal tissue in vitro", Nature, 470(7332): 105-109 (2011).
Lancaster, M.A. et al. "Organogenesis in a dish: Modeling development and disease using organoid technologies", Science, 345(6194):283 (2014).
Belchior, Gustavo Gross et al. "Stem cells and biopharmaceuticals: Vital roles in the growth of tissue-engineered small intestine", Seminars in Pediatric Surgery, 23(3):141-149 (2014).
Wang, Yuli et al. "A microengineered collagen scaffold for generating a polarized crypt-villus architecture of human small intestinal epithelium", Biomaterials, 128:44-55 (2017).
Extended European Search Report corresponding to European Application No. 16744178.1, dated Jul. 2, 2018, 7 pages.
Written Opinion and International Search Report corresponding to International Application No. PCT/US2016/015631, dated May 26, 2016, 4 pages.

(56) References Cited

OTHER PUBLICATIONS

G. L. Eastwood and J. S. Trier. Organ culture of human rectal mucosa. Gastroenterology, 1973, 64(3), 375-382.
H. Autrup, L. A. Barrett, F. E. Jackson, M. L. Jesudason, G. Stoner, P. Phelps, B. F. Trump and C. C. Harris. Explant culture of human colon. Gastroenterology, 1978, 74, 1248-1257.
C. Booth, S. Patel, G. R. Bennion and C. S. Potten. The isolation and culture of adult mouse colonic epithelium. Epithelial Cell Biol., 1995, 4, 76-86.
R. H. Whitehead, A. Brown and P. S. Bhathal. A method for the isolation and culture of human colonic crypts in collagen gels. In Vitro Cellular & Developmental Biology, 1987, 23, 436-442.
J. B. Seidelin, T. Horn and O. H. Nielsen. Simple and efficient method for isolation and cultivation of endoscopically obtained human colonocytes. Am. J. Physiol.-Gastroint. Liver Physiol., 2003, 285, G1122-G1128.
A. Quaroni. Short-term primary culture of epithelial cells from human colon. Gastroenterology, 1989, 96, 535-536.
T. Sato, R. G. Vries, H. J. Snippert, M. van de Wetering, N. Barker, D. E. Stange, J. H. van Es, A. Abo, P. Kujala, P. J. Peters and H. Clevers. Single Lgr5 stem cells build crypt-villus structures in vitro without a mesenchymal niche. Nature, 2009, 459, 262-U147.
T. Sato, J. H. van Es, H. J. Snippert, D. E. Stange, R. G. Vries, M. van den Born, N. Barker, N. F. Shroyer, M. van de Wetering and H. Clevers. Paneth Cells constitute the niche for Lgr5 stem cells in intestinal crypts. Nature. 2011; 469 (7330P: 415-418.
T. Sato, D. E. Stange, M. Ferrante, R. G. Vries, J. H. Van Es, S. Van den Brink, W. J. Van Houdt, A. Pronk, J. Van Gorp, P. D. Siersema and H. Clevers. Long-term expansion of epithelial organoids from human colon, adenoma, adenocarcinoma, and Barrett's epitheiuum. Gastroenterology, 2011, 141, 1762-1772.
P. Jung, T. Sato, A. Merlos-Suarez, F. M. Barriga, M. Iglesias, D. Rossell, H. Auer, M. Gallardo, M. A. Blasco, E. Sancho, H. Clevers and E. Batlle. Isolation and in vitro expansion of human colic stem cells. Nature Medicine, 2011, 17, 1225-1227.
S. Yui, T. Nakamura, T. Sato, Y. Nemoto, T. Mizutani, X. Zheng, S. Ichinose, T. Nagaishi, R. Okamoto, K. Tsuchiya, H. Clevers and M. Watanabe. Functional engraftment of colon epithelium expanded in vitro from a single adult Lgr5+ stem cell. Nature Medicine, 2012, 18, 618-623.
Y. L. Wang, A. A. Ahmad, C. E. Sims, S. T. Magness and N. L. Allbritton. In vitro generation of colonic epithelium from primary cells guided by microstructures. Lab Chip, 2014, 14, 1622-1631.
C. Moon, K. L. VanDussen, H. Miyoshi and T. S. Stappenbeck. Development of a primary mouse intestinal epithelial cell monolayer culture system to evaluate factors that modulate IgA transcytosis. Mucosal Immunol, 2014, 7, 818-828.
K. L. VanDussen, J. M. Marinshaw, N. Shaikh, H. Miyoshi, C. Moon, P. I. Tarr, M. A. Ciorba and T. S. Stappenbeck. Development of an enhanced human gastrointestinal epithelial culture system to facilitate patient-based assays. Gut. 2014; 164: 911-920.
X. Yin, H. F. Farin, J. H. van Es, H. Clevers, R. Langer and J. M. Karp. Niche-independent high-purity cultures of Lgr5+ intestinal stem cells and their progeny. Nature Methods, 2014, 11, 106-112.
H. J. Kim, D. Huh, G. Hamilton and D. E. Ingber. Human gut-on-a-chip inhabited by microbial flora that experiences intestinal peristalsis-like motions and flow. Lab Chip, 2012, 12, 2165-2174.
Q. Ramadan, H. Jafarpoorchekab, C. B. Huang, P. Silacci, S. Carrara, G. Koklu, J. Ghaye, J. Ramsden, C. Ruffert, G. Vergeres and M. A. M. Gijs. NutriChip: nutrition analysis meets microfliudics. Lab Chip, 2013, 13, 196-203.
J. H. Sung, J. J. Yu, D. Luo, M. L. Shuler and J. C. March. Microscale 3-D hydrogel scaffold for biomimetic gastrointestinal (GI) tract model. Lab Chip, 2011, 11, 389-392.
J. H. Sung, M. B. Esch, J. M. Prot, C. J. Long, A. Smith, J. J. Hickman and M. L. Shuler, Microfabricated mammalian organ systems and their integration into models of whole animals and humans. Lab Chip, 2013, 13(7), 1201-1212.
International Search Report corresponding to International Application No. PCT/US19/33955 dated Aug. 15, 2019.

International Search Report corresponding to International Application No. PCT/US2019/032393 dated Jul. 23, 2019.
Speer et al., "Molecular transport through primary human small intestinal monolayers by culture on a collagen scaffold with a gradient of chemical cross-linking", Journal of Biological Engineering (Apr. 27, 2019).
Wang et al., "Formation of Human Colonic Crypt Array by Application of Chemical Gradients Across a Shaped Epithelial Monolayer", Cellular and Molecular Gastroenterology and Hepatology. vol. 5, No. 2, pp. 113-130 (Nov. 3, 2017).
A. DeWard, J. Cramer, and E. Lagasse, Cellular heterogeneity in the mouse esophagus implicates the 30 presence of a nonquiescent epithelial stem cell population, Cell. Rep. 9(2), 701-711 (Oct. 23, 2014).
A. Gracz et al., CD24 and CD44 Mark Human Intestinal Epithelial Cell Populations with Characteristics of Active and Facultative Stem Cells, Stem Cells 31(9), 2024-30 (2013).
A. L. Paguirigan and D. J. Beebe, Nat Protoc, 2007, 2, 1782-1788.
Bo Liu et al. Chemistry of Periodate-Mediated Cross-Linking of 3.4-Dihydroxylphenylalanine (DOPA)-Containing Molecules to Proteins, J Am Chem Soc. 2006; 29:15228-15235, p. 8.
C. Kosinski, V. S. W. Li, A. S. Y. Chan, J. Zhang, C. Ho, W. Y. Tsui, T. L. Chan, R. C. Mifflin, D. W. Powell, S. T. Yuen, S. Y. Leung and X. Chen, Proc. Natl. Acad. Sci. U S. A., 2007, 104, 15418-15423.
C. R. Yang, Bull. Mat. Sci, 2012, 35, 913-918.
D.R. Donohoe, N. Garge, X. X. Zhang, W. Sun, T. M. O'Connell, M. K. Bunger and S. J. Bultman, Cell Metabolism, 2011, 13, 517-526.
E. Fuchs and T. Chen, Embo Reports, 2013, 14, 39-48.
E. J. Formeister, A. L. Sionas, D. K. Lorance, C. L. Barkley, G. H. Lee and S. T. Magness, Am. J Physiol.-Gastroint. Liver Physiol., 2009, 296, G 1108-G 1118.
F. Wang et al., Isolation and Characterization of Intestinal Stem Cells Based on Surface Marker Combinations and Colony-Formation Assay Gastroenterology 145(2), 383-95 (2013).
Gonzalez S et al. A 3D Culture System Enhances the Ability of Human Bone Marrow Stromal Cells to Support the Growth of Limbal Stem/Progenitor Cells, Stem Cell Res. 2016, 16(2):358-364, p. 2,3.
Hai-Long Li et al. The Effect of Amino Density on the Attachment, Migration, and Differentiation of Rat Neural Stem Cells In Vitro, Mol Cells. 2013; 35:436-443. pp. 436, 437, 441.
International Search Report corresponding to International Application No. PCT/US2016/015631 dated May 26, 2016.
International Search Report corresponding to International Application No. PCT/US2017/043601 dated Nov. 16, 2017.
J. Mills and R. Shivdasani, Gastric epithelial stem cells, Gastroenterology 140(2), 412-424 (Feb. 2011).
J. R. Davie, Journal of Nutrition, 2003, 133, 2485S-2493S.
Levenberg S, et al. Differentiation of human embryonic stem cells on threedimensional polymer scaffolds, PNAS. 2003, 100(22): 12741-12746, p. 12741.
M. A. Cayo, A. K. Cayo, S. M. Jarjour and H. Chen, American Journal of Translational Research, 2009, 1, 178-183.
M. Brittan and N. A. Wright, Gut, 2004, 53, 899-910.
M. Hovakimyan, R. F. Guthoff and O. Stachs, Journal of Ophthalmology, 2012, 2012, Article ID 406850.
M. Stelzner, M. Helmrath, J. C. Y. Dunn, S. J. Henning, C. W. Houchen, C. Kuo, J. Lynch, L. H. Li, S. T. Magness, M. G. Martin, M. H. Wong, J. Yu and N. I. H. I. S. C. Consortiu, Am. J Physiol.-Gastroint. Liver Physiol., 2012, 302, G1359-G1363.
Maina JN. Structure, function and evolution of the gas exchangers: comparative perspectives, J Anat. 2002, 201:281-304, p. 300.
N. Barker, M. van de Wetering and H. Clevers, Genes & Development, 2008, 22, 1856-1864.
N. Seyedhassantehrani, Y. Li and L. Yao, Integrative Biology, 2016.
Park YB et al. Alterations of proliferative and differentiation potentials of human embryonic stem cells during long-term culture, Exp Mol Med. 2008, 40(1):98-108, p. 1.
Pedron S. et al. Microfluidic approaches for the fabrication of gradient crosslinfed networks based on poly(ethylene glycol) and hyperbranched polymers for manipulation of cell interactions, J Biomed Mat Res. 2011; 96(1):196-203, p. 197.

(56) References Cited

OTHER PUBLICATIONS

S. Umar, Intestinal Stem Cells, Curr. Gastroenterol Rep. 12(5), 340-348 (Oct. 2010).
Seo JB et al. Epithelial monolayer culture system for real-time single-cell analyses, Phys Rep. 2014, 2(4):e12002, p. 1-3.
Simon AK et al. Polymer-Based Mesh as Supports for Multi-layered 3D Cell Culture and Assays, Biomaterials. 2014; 35(1):1-21, abstract.
Soofi, S.S. et al., Journal of Structural Biology 167, 216-219 (2009).
Szymanski P et al. Adaptation of High-Throughput Screening in Drug Discovery—Toxicological Screening Tests, Int J Mol Sci. 2012, 13:427-452, abstract.
T. Sato, J. H. van Es, H.J. Snippert, D. E. Stange, R. G. Vries, M. van den Born, N. Barker, N. F. Shroyer, M. van de Wetering and H. Clevers, Nature, 2010.
T. Yen and N. Wright, The gastrointestinal tract stem cell niche, Stem Cell Rev. 2(3), 203-212 (2006).
Y. W. Liu, L. H. Gan, D. J. Carlsson, P. Fagerholm, N. Lagali, M. A. Watsky, R. Munger, W. G. Hodge, D. Priest and M. Griffith, Invest. Ophthalmol. Vis. Sci., 2006, 47, 1869-1875.
Boccellato et al., "Polarised epithelial monolayers of the gastric mucosa reveal insights into mucosal homeostasis and defence against infection," Gut, Feb. 7, 2018 (Feb. 7, 2018), vol. 68, pp. 400-413.
Costello et al., "Synthetic Small Intestinal Scaffolds for Improved Studies of Intestinal Differentiation," Biotechnology and Bioengineering, vol. 111, No. 6, Jun. 2014. pp. 1222-1232.
Donohoe et al., "The Warburg Effect Dictates the Mechanism of Butyrate-Mediated Histone Acetylation and Cell Proliferation," Molecular Cell, vol. 48 pp. 612-626 (2012).
Gaudier et al., "Butyrate specifically modulates MUC gene expression in intestinal epithelial goblet cells deprived of glucose," Am J. Physiol Gastrointest Liver Physiol., vol. 287: G1168-G1174 (2004).
International Search Report corresponding to International Application No. PCT/US2019/061743 dated Feb. 11, 2020.
Office Action corresponding to Japanese Patent Application No. 2017540628 dated Jan. 7, 2020.
Cummings et al. "Properties of engineered vascular constructs made from collagen, fibrin, and collagen-fibrin mixtures," Biomaterials 25, 3699-3706 (2004).
Donohoe et al., "The Warburg Effect Dictates the Mechanism of Butyrate-Mediated Histone Acetylation and Cell Proliferation," Supplemental Information, Molecular Cell, vol. 48, 258 pages (2012).
Song et al. "Collagen scaffolds derived from a marine source and their biocompatibility," Biomaterials, 27, 2951-2961 (2006).
Sundararaghavan et al. "Genipin-induced changes in collagen gels: Correlation of mechanical properties to fluorescence," Journal of Biomedical Materials Research Part A, 87A, 308-320 (2008).
Yoo et al. "Effects of Schisandra Lignans on P-Glycoprotein-Mediated Drug Efflux in Human Intestinal Caco-2 Cells," Planta Med., 73, 444-450 (2007).
International Preliminary Report on Patentability corresponding to International Application No. PCT/US2016/015631 dated Aug. 1, 2017.
International Preliminary Report on Patentability corresponding to International Application No. PCT/US2017/043601 dated Jan. 29, 2019.
International Preliminary Report on Patentability corresponding to International Application No. PCT/US2019/032393 dated Nov. 17, 2020.
International Preliminary Report on Patentability corresponding to International Application No. PCT/US2019/033955 dated Dec. 1, 2020.
Orban et al. "Crosslinking of collagen gels by transglutaminase," Journal of Biomedical Materials Research Part A, 68A, 756-762 (2004).
VanDussen et al. "Development of an enhanced human gastrointestinal epithelial culture system to facilitate patient-based assays," Gut, vol. 64, pp. 911-920 (2015).
Kaminsky et al. "Small Intestinal Cytochromes P450," Critical Reviews in Toxicology 21, 407-422 (1992).
Damink et al. "Glutaraldehyde as a crosslinking agent for collagen-based biomaterials," Journal of Materials Science: Materials in Medicine, 6, 460-472 (1995).
Martignoni et al., Abstract of "An in vivo and in vitro comparison of CYP induction in rat liver and intestine using slices and quantitative RT-PCR," Chemico-Biological Interactions, vol. 151, Iss. 1, pp. 1-11 (2004), 19 pages.
Martignoni "Species and strain differences in drug metabolism in liver and intestine," University of Groningen/UMCG, 1-136 (2006).
Matsuzawa A et al. Construction of three-dimensional liver tissue models by cell accumulation technique and maintaining their metabolic functions for long-term culture without medium change, J Biomed Mater Res Part A. 2014, p. 1, Apr. 2015:103(4):1554-64.
Moon et al., "Development of a primary mouse intestinal epithelial cell monolayer culture system to evaluate factors that modulate IgA transcytosis," Mucosal Immunology, vol. 7, No. 4, pp. 818-828 (2014).
Vrana et al. "EDC/NHS cross-linked collagen foams as scaffolds for artificial corneal stroma," Journal of Biomaterials Science-Polymer Edition, vol. 18, No. 12, pp. 1527-1545 (2007).
Office Action corresponding to European Patent Application No. 16744178.1 dated Nov. 11, 2020.
Office Action corresponding to Japanese Patent Application No. 2017540628 dated Nov. 4, 2020.
Office Action (Restriction Requirement) corresponding to U.S. Appl. No. 16/316,139 dated Feb. 4, 2021.
Shah et al. "Role of Caco-2 cell monolayers in prediction of intestinal drug absorption," Biotechnol. Prog. 22: 186-198 (2006).
Szpak, "Fish bone chemistry and ultrastructure: implications for taphonomy and stable isotope analysis," J. Archaeol. Sci, 38, 3358-3372 (2011).
Paine et al. "Cytochrome P-450 1A1 Expression in Human Small Bowel: Interindividual Variation and Inhibition by Ketoconazole," Drug Metabolism and Disposition, vol. 27, No. 3, pp. 360-364 (1999).
Roeder et al. "Compliance, elastic modulus, and burst pressure of small-intestine submucosa (SIS), small-diameter vascular grafts," J Biomed Mater Res. 47, 65-70 (1999).
Rosa Acp et al. Interaction of *Escherichia coli* strains of non-EPEC serogroups that carry eae and lack the EAF and stx gene sequences with undifferentiated and differentiated intestinal human Caco-2 cells, FEMS Microbiology Letters. 2001, 200: 117-122, p. 118.
Written Opinion and International Search Report corresponding to International Application No. PCT/US2017/043601 dated Nov. 16, 2017.
Written Opinion of the International Searching Authority corresponding to International Application No. PCT/US2019/032393 dated Jul. 23, 2019.
Written Opinion of the International Searching Authority corresponding to International Application No. PCT/US2019/033955 dated Aug. 15, 2019.
Written Opinion of the International Searching Authority corresponding to International Application No. PCT/US2019/061743 dated Feb. 11, 2020.
Di et al. "Collagen stabilization and modification using a polyepoxide, triglycidyl isocyanurate," Polymer Degradation and Stability, 94, 1684-1692 (2009).
Boccellato et al. "Polarised epithelial monolayers of the gastric mucosa reveal insights into mucosa! homeostasis and defence against infection," Gut, Feb. 7, 2018 (Feb. 7, 2018), vol. 68, pp. 400-413.
Wang et al. "Building a Thick Mucus Hydrogel Layer to Improve the Physiological Relevance of In Vitro Primary Colonic Epithelial Models," Cellular and Molecular Gastroenterology and Hepatology, Jul. 26, 2019 (Jul. 26, 2019), vol. 8, Iss. 4, pp. 653-655.
Wang et al. "Capture and 3D culture of colonic crypts and colonoids in a microarray platform," Lab Chip, The Royal Society of Chemistry, vol. 13, pp. 4625-4634 (2013b).
Written Opinion corresponding to International Application No. PCT/US2016/015631 dated May 26, 2016.

(56) References Cited

OTHER PUBLICATIONS

Yeste et al. "Engineering and monitoring cellular barrier models," Journal of Biological Engineering, Sep. 12, 2018 (Sep. 12, 2018), vol. 12, No. 18, pp. 1-19.
Extended European Search Report corresponding to European Patent Application No. 17835084.9 dated Mar. 5, 2020.
Kharkar et al. (2013), "Designing degradable hydrogels for orthogonal control of cell microenvironments," Chem. Soc. Rev., vol. 42, pp. 7335-7372. (Year: 2013).
Notice of Publication corresponding to European Patent Application No. 17835084.9-1120 dated May 8, 2019.
Notice of Publication corresponding to European Patent Application No. 19804471.1 dated Feb. 24, 2021.
Notice of Publication corresponding to European Patent Application No. 19806626.8-1111 dated Mar. 17, 2021.
Office Action corresponding to U.S. Appl. No. 16/316,139 dated Apr. 28, 2021.
Ahmad et al., "Optimizing Wnt-3a and R-spondin1 concentrations for stem cells: critical drivers of epithelial homeostasis and regeneration." Nature reviews molecular cell biology vol. 15, pp. 19, (2014).
Barkla et al. "The fate of epithelial cells in the human large intestine." Pathology vol. 31, pp. 230-238, (1999).
Bartfeld, "Modeling infectious diseases and host-microbe interactions in gastrointestinal organoids." Developmental biology, vol. 420, pp. 262-270, (2016).
Basak et al., "Induced quiescence of Lgr5+ stem cells in intestinal organoids enables differentiation of hormone-producing enteroendocrine cells." Cell Stem Cell, vol. 20, pp. 177-190 e4, (2017).
Dekkers et al., "A functional CFTR assay using primary cystic fibrosis intestinal organoids." Nature medicine, vol. 19, p. 939, (2013).
Finkbeiner et al., "Stem cell-derived human intestinal organoids as an infection model for rotaviruses." MBio vol. 3, e00159-12, (2012).
Gamet et al., "Effects of short-chain fatty acids on growth and differentiation of the human colon-cancer cell line HT29." International Journal of Cancer vol. 52, pp. 286-289. (1992).
Gattazzo et al., "Extracellular matrix: a dynamic microenvironment for stem cell niche." Biochimica et Biophysica Acta (BBA)—General Subjects, vol. 1840, pp. 2506-2519, (2014).
Hall et al., "Human genetic variation and the gut microbiome in disease." Nature Reviews Genetics vol. 18, p. 690, (2017).
In et al., "Enterohemorrhagic *Escherichia coli* reduces mucus and intermicrovillar bridges in human stem cell-derived colonoids." Cellular and molecular gastroenterology and hepatology vol. 2, pp. 48-62 e3, (2016).
Ito et al., "Metabolism and the control of cell fate decisions and stem cell renewal." Annual review of cell and developmental biology. vol. 32, pp. 399-409, (2016).
Kaiko et al., "The colonic crypt protects stem cells from microbiota-derived metabolites." Cell vol. 165, pp. 1708-1720, (2016).
Karve et al., "Intestinal organoids model human responses to infection by commensal and Shiga toxin producing *Escherichia coli*." PloS one vol. 12, e0178966, (2017).
Kozuka et al., "Development and Characterization of a Human and Mouse Intestinal Epithelial Cell Monolayer Platform." Stem cell reports vol. 9, pp. 1976-1990, (2017).
Li et al., "Role of mechanical factors in fate decisions of stem cells." Regenerative medicine vol. 6, pp. 229-240, (2011).
Semrau et al., "Studying lineage decision-making in vitro; emerging concepts and novel tools." Annual review of cell and developmental biology vol. 31, pp. 317-345, (2016).
Shreiner et al., "The gut microbiome in health and in disease." Current opinion in gastroenterology vol. 31, p. 69, (2015).
Terryn et al., "Recent advances in lineage differentiation from stem cells: hurdles and opportunities?" F1000Resarch vol. 7, (2018).
Tong et al., "Towards a defined ECM and small molecule based monolayer culture system for the expansion of mouse and human intestinal stem cells." Biomaterials vol. 154, pp. 60-73, (2018).
Tremlett et al., "The gut microbiome in human neurological disease: a review." Annals of Neurology, (2017).
Tsubouchi, "Kinetic analysis of epithelial cell migration in the mouse descending colon." Developmental Dynamics, vol. 161, pp. 239-246, (1981).
Van Es et al., "Dll1 + secretory progenitor cells revert to stem cells upon crypt damage." Nature cell biology vol. 14, p. 1099, (2012).
Wang et al., "A microengineered collagen scaffold for generating a polarized crypt-villus architecture of human small intestinal epithelium." Biomaterials vol. 128, pp. 44-55, (2017).
Wang et al., "Formation of human colonic crypt array by application of chemical gradients across a shaped epithelial monolayer." Cellular and molecular gastroenterology and hepatology vol. 5, pp. 113-130, (2018).
Wang et al., "In vitro Generation of Mouse Colon Crypts." ACS biomaterials science & engineering vol. 3, pp. 2502-2513, (2017).
Whitehead et al., "Effects of short-chain fatty acids on a new human colon carcinoma cell line (LIM1215)." Gut, vol. 27, pp. 1457-1463, (1986).
Young, "The role of the microbiome in human health and disease: an introduction for clinicians." BMJ vol. 356, j831, (2017).
Xu et al., "Butyrate induces apoptosis by activating PDC and inhibiting complex I through SIRT3 inactivation." Signal Transduction and Targeted Therapy, vol. 2, pp. e16035, (2017).
Ruemmele et al., "Butyrate induced Caco-2 cell apoptosis is mediated via the mitochondrial pathway." Gut, vol. 52, pp. 94-100, (2003).
Koh et al., "From Dietary Fiber to Host Physiology: Short-Chain Fatty Acids as Key Bacterial Metabolites." Cell, vol. 165, pp. 1332-1345, (2016).
Barker, "Adult intestinal stem cells: critical drivers of epithelial homeostasis and regeneration." Nature Reviews Molecular Cell Biology, vol. 15, p. 19, (2014).
Sternini et al., "Enteroendocrine cells: a site of 'taste' in gastrointestinal chemosensing." Current Opinion in Endocrinology, Diabetes, and Obesity, vol. 15, p. 73, (2008).
Birchenough et al., "A sentinel goblet cell guards the colonic crypt by triggering Nlrp6-dependent Muc2 secretion." Science, vol. 352, pp. 1535-1542, (2016).
Valenta et al., "The many faces and functions of β-catenin." The EMBO Journal, vol. 31, pp. 2714-2736, (2012).
Provenzano and Keely, J. Cell Sci, vol. 124, pp. 1195-1205, (2011).
Yim and Sheetz, "Force-dependent cell signaling in stem cell differentiation." Stem Cell Research & Therapy, vol. 3, p. 41, (2012).
Lü et al., "Differential regulation of morphology and sternness of mouse embryonic stem cells by substrate stiffness and topography," Biomaterials, vol. 35, pp. 3945-3955, (2014).
Chowdhury et al., "Soft Substrates Promote Homogeneous Self-Renewal of Embryonic Stem Cells via Downregulating Cell-Matrix Tractions." PloS one, vol. 5, e15655, (2010).
Rother et al., "Cytoskeleton remodelling of confluent epithelial cells cultured on porous substrates." Journal of the Royal Society Interface, vol. 12, 20141057, (2015).
Hayman et al., "Growth of human stem cell-derived neurons on solid three-dimensional polymers." Journal of Biochemical and Biophysical Methods, vol. 62, pp. 231-240, (2005).
Peyton et al., "Marrow-Derived Stem Cell Motility in 3D Synthetic Scaffold is Governed by Geometry Along With Adhesivity and Stiffness." Biotechnology and Bioengineering, vol. 108, pp. 1181-1193, (2011).
Ahmad et al., "Optimizing Wnt-3a and R-spondin1 concentrations for stem cell renewal and differentiation in intestinal organoids using a gradient-forming microdevice." RSC Advances, vol. 5, p. 74881-74891, (2015).
Franck et al., "Three-Dimensional Traction Force Microscopy: A New Tool for Quantifying Cell-Matrix Interactions." PloS one, vol. 6, e17833, (2011).
Qu et al., "Maturation State and Matrix Microstructure Regulate Interstitial Cell Migration in Dense Connective Tissues." Scientific Reports, vol. 8, 3295, (2018).

(56) References Cited

OTHER PUBLICATIONS

Vallo et al., "Elastic Modulus and Yield Stress of Epoxy Networks in the Glassy State." Polymer Gels and Networks, vol. 1, pp. 257-266, (1993).
Engelberg and Tesoro, "Mechanical and Thermal Properties of Epoxy Resins With Reversible Crosslinks," Polymer Engineering & Science, vol. 30, pp. 303-307, (1990).
Faul et al., "G*Power 3: A flexible statistical power analysis program for the social, behavioral, and biomedical sciences," Behavior Research Methods, vol. 39, pp. 175-191, (2007).
Schindelin et al., "Fiji—an Open Source platform for biological image analysis." Nature Methods, vol. 9, p. 676, (2012).
Pai et al., "Photoresist with Low Fluorescence for Bioanalytical Applications," Analytical Chemistry, vol. 79, pp. 8774-8780, (2007).
Allen et al., "Adherent and soluble Mucus in the Stomach and Duodenum." Digestive Diseases and Sciences vol. 30, 55S-62S, (1985).
Pelaseyed et al., "The mucus and mucins of the goblet cells and enterocytes provide the first defense line of the gastrointestinal tract and interact with the immune system." Immunological reviews vol. 260, pp. 8-20, (2014).
Murgia et al., "The role of mucus on drug transport and its potential to affect therapeutic outcomes." Adv Drug Deliv Rev vol. 124, pp. 82-97, (2018).
Lehr et al., "An estimate of turnover time of intestinal mucus gel layer in the rat in situ loop." International Journal of Pharmaceutics vol. 70 pp. 235-240, (1991).
Wei et al., "Fatty Acid Synthase Modulates Intestinal Barrier Function through Palmitoylation of Mucin 2." Cell Host & Microbe vol. 11, pp. 140-152, (2012).
Johansson et al., "The inner of the two Muc2 mucin-dependent mucus layers in colon is devoid of bacteria." Proceedings of the National Academy of Sciences of the United States of America, vol. 105, pp. 15064-15069, (2008).
Hansson, "Role of mucus layers in gut infection and inflammation." Current Opinion in Microbiology vol. 15, pp. 57-62, (2012).
Carlson et al., "Engineering the Mucus Barrier." Annual Review of Biomedical Engineering vol. 20, pp. 197-220,(2018).
Werlang et al., "Engineering mucus to study and influence the microbiome." Nature Reviews Materials vol. 4, pp. 134-145, (2019).
Rogier et al., "Secretory IgA is Concentrated in the Outer Layer of Colonic Mucus along with Gut Bacteria." Pathogens vol. 3, pp. 390-403, (2014).
Gunasekara et al., "A Monolayer of Primary Colonic Epithelium Generated on a Scaffold with a Gradient of Stiffness for Drug Transport Studies." Analytical Chemistry vol. 90, pp. 13331-13340, (2018).
Quigley, "Gut bacteria in health and disease." Gastroenterology & hepatology vol. 9, pp. 560-569, (2013).
Lesuffleur et al., "Growth adaptation to methotrexate of HT-29 human colon carcinoma cells is associated with their ability to differentiate into columnar absorptive and mucus-secreting cells." Cancer Research vol. 50, pp. 6334-6343, (1990).
Nusrat et al., "Clostridium difficile Toxins Disrupt Epithelial Barrier Function by Altering Membrane Microdomain Localization of Tight Junction Proteins." Infection and Immunity vol. 69, pp. 1329-1336, (2001).
Sato et al., "Single Lgr5 stem cells build crypt-villus structures in vitro without a mesenchymal niche." Nature vol. 459, pp. 262-U147, (2009).
Date et al., "Mini-Gut Organoids: Reconstitution of Stem Cell Niche." Annual Review of Cell and Developmental Biology vol. 31, pp. 269-289, (2015).
Sato et al., "Long-term Expansion of Epithelial Organoids From Human Colon, Adenoma, Adenocarcinoma, and Barrett's Epithelium." Gastroenterology vol. 141, pp. 1762-1772, (2011).
Fatehullah et al., "Cell and tissue polarity in the intestinal tract during tumourigenesis: cells still know the right way up, but tissue organization is lost." Philosophical Transactions of the Royal Society B-Biological Sciences vol. 368, 20130014, (2013).

Noel et al., "A primary human macrophage-enteroid co-culture model to investigate mucosal gut physiology and host pathogen interactions." Scientific Reports vol. 7, p. 45270, (2017).
Puzan et al., "Enteric Nervous System Regulation of Intestinal Stem Cell Differentiation and Epithelial Monolayer Function." Scientific Reports vol. 8, p. 6313, (2018).
Wang et al., "Analysis of Interleukin 8 Secretion by a Stem-Cell-Derived Human-Intestinal-Epithelial-Monolayer Platform." Analytical Chemistry vol. 90, pp. 11523-11530, (2018).
Whitcutt et al., "A biphasic chamber system for maintaining polarity of differentiation of cultured respiratory tract epithelial cells." In Vitro Cellular & Developmental Biology, vol. 24, pp. 420-428, (1988).
Raredon et al., "A Rotating Bioreactor for Scalable Culture and Differentiation of Respiratory Epithelium." Cell Medicine vol. 7, pp. 109-121, (2012).
O'Boyle et al., "Temporal dynamics of ovine airway epithelial cell differentiation at an air-liquid interface." Plos One vol. 12, e0181583, (2017).
Ootani et al., "An air-liquid interface promotes the differentiation of gastric surface mucous cells (GSM06) in culture." Biochemical and Biophysical Research Communications vol. 271, pp. 741-746, (2000).
Yokoyama et al., "Differentiation of gastric surface mucous cells (GSM06) induced by air-liquid interface is regulated partly through mitogen-activated protein kinase pathway." Journal of Gastroenterology and Hepatology, vol. 22, pp. 2310-2315, (2007).
Navabi et al., "Gastrointestinal Cell Lines Form Polarized Epithelia with an Adherent Mucus Layer when Cultured in Semi-Wet Interfaces with Mechanical Stimulation." Plos One vol. 8, e68761, (2013).
Elkins et al., "Mechanisms and applications of hypertonic saline." Journal of the Royal Society of Medicine, vol. 104, pp. S2-S5, (2011).
Lüdeking et al., "Osmotic changes and ethanol modify TFF gene expression in gastrointestinal cell lines." Febs Letters vol. 439, pp. 180-184, (1998).
Shields et al., "Absorption and secretion of water and electrolytes by the intact colon in a patient with primary aldosteronism." British Medical Journal vol. 1, pp. 93-96, (1968).
Wapnir et al., "Regulation mechanisms of intestinal secretion: implications in nutrient absorption." The Journal of Nutritional Biochemistry vol. 13, pp. 190-199, (2002).
Koch et al., "Plasma vasoactive intestinal polypeptide concentration determination in patients with diarrhea." Gastroenterology vol. 100, pp. 99-106, (1991).
Schwartz et al., "Vasoactive intestinal peptide stimulation of adenylate cyclase and active electrolyte secretion in intestinal mucosa." Journal of Clinical Investigation vol. 54, pp. 536-544, (1974).
Wu et al., "Vasoactive Intestinal Polypeptide Promotes Intestinal Barrier Homeostasis and Protection Against Colitis in Mice." Plos One vol. 10, e0125225, (2015).
Johansson et al., "Bacteria penetrate the normally impenetrable inner colon mucus layer in both murine colitis models and patients with ulcerative colitis." Gut, vol. 63, pp. 281-291, (2014).
Bernstam et al., "Keratinocytes grown at the air-liquid interface." In Vitro Cellular & Developmental Biology vol. 22, pp. 695-705, (1986).
Ootani et al., "Sustained in vitro intestinal epithelial culture within a Wnt-dependent stem cell niche." Nature Medicine vol. 15, p. 1-U140, (2009).
Voth et al., "Clostridium difficile toxins: mechanism of action and role in disease." Clinical microbiology reviews vol. 18, pp. 247-263, (2005).
He et al., "Clostridium difficile toxin A triggers human coloncyte IL-8 release via mitochondrial oxygen radical generation." Gastroenterology, vol. 122, pp. 1048-1057, (2002).
Mahida et al., "Effect of Clostridium difficile toxin A on human intestinal epithelial cells: induction of interleukin 8 production and apoptosis after cell detachment." Gut vol. 38, pp. 337-347, (1996).
Haller et al., "Non-pathogenic bacteria elicit a differential cytokine response by intestinal epithelial cell/leucocyte co-cultures." Gut vol. 47, pp. 79-87, (2000).

(56) References Cited

OTHER PUBLICATIONS

Parlesak et al., "Modulation of Cytokine Release by Differentiated CACO-2 Cells in a Compartmentalized Coculture Model with Mononuclear Leucocytes and Nonpathogenic Bacteria." Scandinavian Journal of Immunology vol. 60, pp. 477-485, (2004).
English Translation of Notice of Allowance corresponding to JP Patent Application No. JP 2017-540628 dated Jun. 29, 2021.
English Translation of First Office Action corresponding to JP Patent Application No. JP 2019-504019 dated May 25, 2021.

* cited by examiner

METHODS TO GENERATE GASTROINTESTINAL EPITHELIAL TISSUE CONSTRUCTS

RELATED APPLICATIONS

This application is a 35 U.S.C. § 371 national phase application international Application Serial No. PCT/US2016/015631, filed Jan. 29, 2016, which claims the benefit of United States Provisional Patent Application Serial No. 62/110,147, filed Jan. 30, 2015, the disclosure of each of which is incorporated by reference herein in its entirety.

GOVERNMENT SUPPORT

This invention was made with Government support under Grant number EY024556 awarded by the National Institutes of Health. The United States Government has certain rights to this invention.

BACKGROUND OF THE INVENTION

Most organs in the body possess an epithelial layer composed of multiple cell types. For example, the mammalian intestine is lined with a single layer of epithelial cells which invaginate into the underlying mesenchyme to form tubular glands (e.g., in the small intestine called "crypts of Lieberkühn"). The proliferative compartments of intestinal epithelium are located at the base of these crypts where the stem cells and transit-amplifying cells reside. These cells fuel the rapid renewal (~5 days in mice[1]) of intestinal epithelial cells on the luminal aspect where most of the non-proliferative cells are positioned.[2] This polarity of cellular organization is thought to be maintained by a balance of biochemical and biophysical in vivo microenvironments, including gradients of soluble factors (e.g. Wnt, BMP, Notch, butyrate) across the basal-luminal axis, and biophysical interactions with supporting cells (e.g. pericryptal fibroblasts) and their secreted extracellular matrices.[3-5]

Culture of live crypts in vitro has been attempted since the 1970s, but it has proven to be extremely difficult to generate a long-term proliferative intestinal epithelium in vitro.[6, 7] This is thought to be a result of the complexity of in vivo microenvironments that constitute the intestinal epithelial stem-cell niche, which has been impossible to recapitulate in vitro. Live intact crypts can be released from animal or human intestine specimens by chelating divalent cations and mechanical agitation.[8-10] Alternatively stem cells from the gut including the large intestine can be isolated by fluorescence-activated cell sorting, magnetic activated cell sorting, or other cell-separation tools after release from the epithelium. Standard 2D culture of crypts in dishes yields short-term growth of a monolayer of cells.[11] Performing 3D culture by embedding crypts or stem cells in collagen gel alone (i.e. without a feeder layer of supporting cells) does not improve crypt survival.[9] The loss of proliferative ability of crypt cells under these culture methods suggests the loss of intestinal stem cells in vitro. This situation was rectified in 2009 when Hans Clevers and colleagues successfully cultured 3D organoids by inclusion of soluble growth factors (Wnt-3A, R-spondin, noggin and epidermal growth factor [EGF]) in the culture milieu. This breakthrough enabled long-term culture of organoids and stem cells derived from the small and large intestines.[12-16] Embedding isolated crypts or isolated stem cells within a 3D extracellular matrix (ECM) with added growth factors has now been shown to support the survival of stem cells and promote 3D proliferative expansion into epithelial organoids.[17] These organoids contain self-renewing stem cells as well as all differentiated cell types present in crypts: goblet cells (secreting mucus), absorptive enterocytes (absorbing water and electrolytes), and enteroendocrine cells (secreting hormones). While this 3D organoid technique is effective in supporting long-term proliferative growth of organoids, it does not precisely mimic the in vivo biochemical and biophysical microenvironments of crypts. An additional limitation is the enclosed spheroid structure of organoids that makes it difficult to study molecular transportation through the epithelial cells and does not recapitulate the exposed surface of the epithelium as occurs in the intact organ.

Biologists have tried to overcome the limitations of the 3D organoid model by revisiting the traditional 2D culture method, aiming to generate a monolayer of intestinal epithelial tissue. The Allbritton group cultured crypts on a solid polydimethylsiloxane (PDMS) surface without embedding the crypts in 3D extracellular matrix.[18] Although supplied with soluble growth factors (Wnt-3A, R-spondin, noggin and EGF), 2D culture of crypts produced only a short-lived, non-proliferative monolayer of cells. The Stappenbeck group dissociated the 3D intestinal organoids, and 2D cultured the dissociated cells on the porous membrane of a Transwell insert to generate a continuous monolayer.[19, 20] However, the cells in the monolayer were composed of fully-differentiated, non-renewing cells. As a result, functional assays using the monolayer could only be performed immediately after setting up the culture as the differentiated cells died within 3 days of plating. These results indicated the loss of stem cell activity in the traditional 2D culture of crypts on a solid surface (even that of a porous membrane). Since these monolayers possessed no stem cells, they were not self-renewing. Therefore, a biochemical microenvironment containing soluble growth factors alone is not enough to sustain stem-cell activity in intestinal epithelium. The biophysical microenvironment (e.g. the surface for cell attachment) is as equivalently important as the biochemical microenvironment in order to sustain the persistence and growth of stem cells.

The lamina propria is the biophysical microenvironment for intestinal stem cells in vivo, and is a thin layer of loose connective tissue on which the stem cells reside. The lamina propria is permeable allowing the transport of factors and nutrition to the epithelium. In addition, the lamina propria is rich in the extracellular matrices laminin and collagen IV. A solid surface (such as composed of polystyrene, polydimethylsiloxane, or the Transwell porous membrane composed of polyester, polycarbonate, etc.) does not fully mimic the lamina propria in terms of permeability, stiffness, and presence of ECM components.

SUMMARY OF THE INVENTION

To overcome the problems noted above in mimicking the lamina propria, biomimetic scaffolds were fabricated from water soluble ECM proteins to create a suitable biophysical microenvironment for maintaining the viability of stem cells.

A first aspect of the invention is a method of making a live cell construct, comprising:

(a) providing a non-cellular support (e.g., a porous support) having a top surface and a bottom surface, (b) contacting live undifferentiated (e.g., stem and/or progenitor cells) cells to the porous non-cellular support, and then (c) propagating a gastrointestinal epithelial cell monolayer on the top surface. The live cells in the monolayer preferably comprise undifferentiated cells, and in some embodiments comprise both differentiated and undifferentiated cells in combination. The monolayer is preferably a long-lived monolayer, as discussed further below.

A second aspect of the present invention is a live cell construct, comprising:

(a) a non-cellular support (e.g., a porous support) having a top surface and a bottom surface (b) a monolayer of live gastrointestinal epithelial cells formed on said top surface. The live cells in the monolayer comprise undifferentiated cells (e.g., stem or progenitor cells), and optionally but in some embodiments preferably, differentiated cells (e.g., enterocytes, goblet cells) in combination with the undifferentiated cells.

A third aspect of the invention is a method of sustaining a live cell construct, comprising:

(a) providing a construct as described above;

(b) contacting a first culture media to the construct top surface; and (c) contacting a second culture media (different from the first culture media) to the construct bottom surface. One of the culture media induces the differentiation of propagating stem and progenitor cells and the other of the culture media induces the propagation of undifferentiated cells.

The present invention is explained in greater detail in the drawings herein and the specification set forth below. Note that, while substantial discussion of embodiments with wells, crypts or lumens is provided, other embodiments of the invention do not require such wells, crypts or lumens. Note also that, while the invention is explained in substantial detail with embodiments where the gastrointestinal epithelial cells are attached to the support, the gastrointestinal epithelial cells can be detached from the support to provide a cell suspension thereof for other uses or purposes (e.g. therapeutics, implantation, drug screening, passage/expansion, cryopreservation, etc.).

DETAILED DESCRIPTION OF THE PREFERRED EMBODIMENTS

Figure 1:
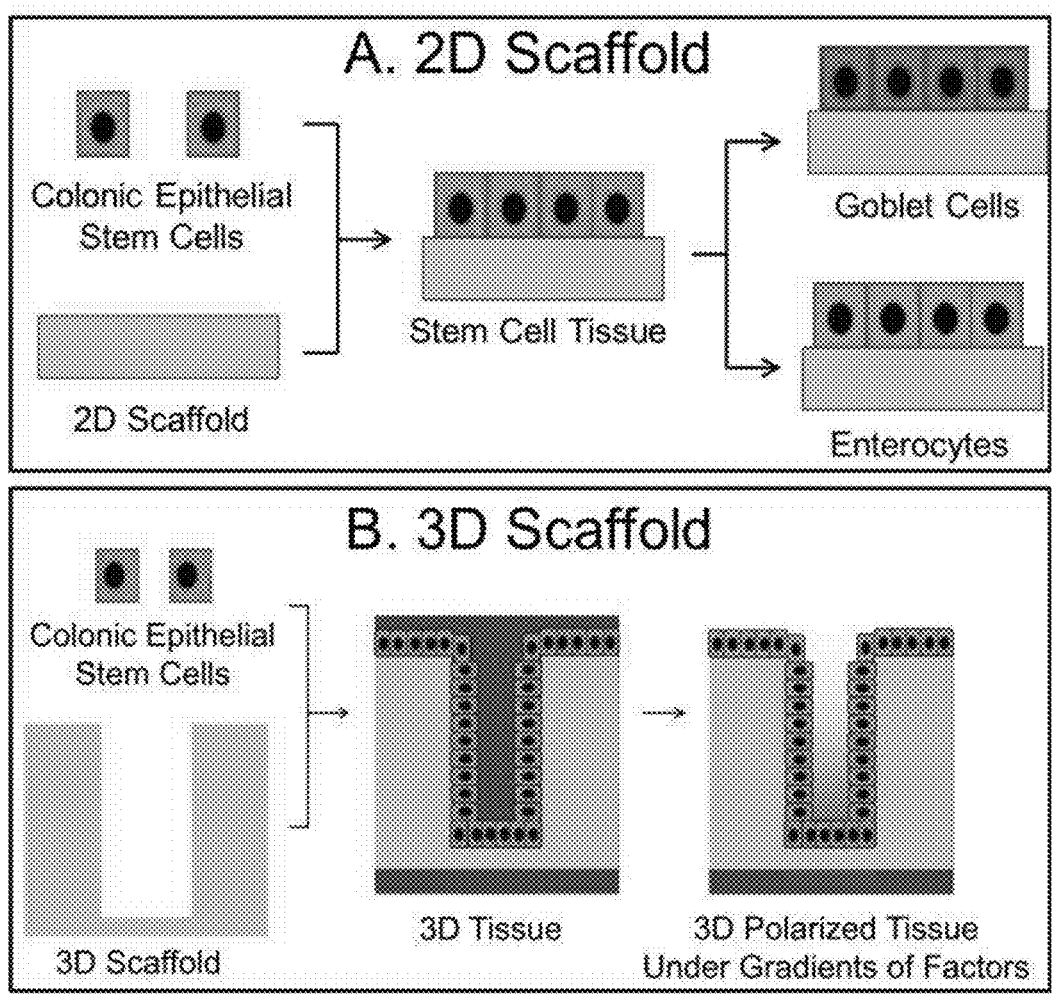
FIG. 1. Schematics of culturing intestinal epithelial stem cells on biomimetic, artificially engineered 2D and 3D scaffolds. (A) 2D scaffold. Epithelial stem cells are plated on a 2D scaffold to form a continuous monolayer of stem cells. Depicted are cells differentiated to two specialized cell types: goblet cells and enterocytes. (B) 3D scaffold. Epithelial stem cells are cultured on a 3D scaffold possessing microwell structures. A 3D tissue is generated and polarized under a gradient of soluble growth factors.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "top," "bottom," "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

1. Gastrointestinal Epithelial Cells.

Cells such as undifferentiated cells and/or gastrointestinal epithelial cells used to carry out the present invention may be of any species of origin, including mammalian, avian, reptile, amphibian, and insect. In some embodiments the cells are mammalian cells, examples of which include but are not limited to as human, monkey, ape, goat, sheep, dog, cat, horse, cow, and pig gastrointestinal epithelial cells. In some embodiments, the cells are preferably derived from primary tissues, and are not cancer or tumor cells. Any type of gastrointestinal epithelial cells may be used, including colon, small intestine, stomach, esophagus, tongue, nasopharynx, oropharynx, laryngeopharynx, and pancreatic epithelial cells.

The gastrointestinal epithelial cells may be undifferentiated cells (e.g., stem or progenitor cells), differentiated cells (e.g., enterocytes, Paneth cells, enteroendocrine cells, tuft cells, microcells, intra-epithelial lymphocytes, and/or goblet cells), or combinations thereof, depending upon the particular stage or time at which the invention is being carried out.

Gastrointestinal epithelial cells, including undifferentiated gastrointestinal epithelial cells (or gastrointestinal epithelial stem cells), are known and may be harvested or provided in accordance with known techniques, or variations thereof that will be apparent to those skilled in the art. See, e.g., T. Yen and N. Wright, The gastrointestinal tract stem cell niche, *Stem Cell Rev.* 2(3), 203-212 (2006); S. Umar, Intestinal Stem Cells, *Curr. Gastroenterol Rep.* 12(5), 340-348 (October 2010); P. Jung et al., Isolation and in vitro expansion of human colonic stem cells, *Nature Medicine* 17, 1225-1227 (2011); J. Mills and R. Shivdasani, Gastric epithelial stem cells, *Gastroenterology* 140(2), 412-424 (February 2011); A. DeWard, J. Cramer, and E. Lagasse, Cellular heterogeneity in the mouse esophagus implicates the presence of a nonquiescent epithelial stem cell population, *Cell. Rep.* 9(2), 701-711 (Oct. 23, 2014); A. Gracz et al., CD24 and CD44 Mark Human Intestinal Epithelial Cell Populations with Characteristics of Active and Facultative Stem Cells, *Stem Cells* 31(9), 2024-30 (2013); F. Wang et al., Isolation and Characterization of Intestinal Stem Cells Based on Surface Marker Combinations and Colony-Formation Assay *Gastroenterology* 145(2), 383-95 (2013).

2. Live Cell Constructs and Methods of Making.

As noted above, the present invention provides live cell constructs and methods of making the same. In general, the methods are carried out by:

(a) providing a non-cellular support having a top surface and a bottom surface, (b) contacting live undifferentiated cells (e.g., stem and/or progenitor cells) to the non-cellular support (typically on the top surface thereof), and then (c) propagating a gastrointestinal epithelial cell monolayer on support (typically on the top surface thereof).

The undifferentiated cells may be of any suitable type, including but not limited to mesenchymal stem cells, hematopoietic stem cells, induced pluripotent stem cells, stem cells obtained from or derived from gastrointestinal epithelia, etc.

The live cells in the monolayer preferably comprise both differentiated cells (e.g., enterocytes, Paneth cells, enteroendocrine cells, tuft cells, microcells, intra-epithelial lymphocytes, and/or goblet cells) and undifferentiated cells (e.g., stem or progenitor cells) in combination (e.g., in a ratio of from 1:10,000, 2:10,000, or 10:10,000, up to 10,000:1, 10:000:2, or 10,000:10). Typically the method further includes the step of:

(d) contacting a culture media to the monolayer of live cells (e.g., which culture media is in or on the support), which culture media sustains the monolayer of live cells. Optionally, but in some embodiments preferably, the culture media will include a short-chain fatty acid (e.g., butyrate, acetate, propionate, valproate, etc.), at a physiologic concentration (e.g., in the range of 0.1-5 mM for the colon). The culture media will also include typical nutrients, growth factors, and signaling factors and the like as discussed further below.

In some embodiments: (i) the culture media contains not more than 10 milliMolar of monosaccharides plus disaccharides (total, in combination); and, at the same time, (ii) the culture media contains at least 2 milliMolar of said short chain fatty acids (e.g. up to 20, 50, or 100 milliMolar of short chain fatty acids total, in combination).

Advantageously, the monolayer may be sustained and propagated for an extended time: that is, a time of at least 2, 4, or 6 days, up to 2 or 4 weeks, or 2 or 4 months, or more.

Supports used in the present invention (sometimes referred to as the extracellular matrix or "ECM") are described in the examples below and the discussion below). The supports may be organic, inorganic, or a composite thereof. In some embodiments the supports comprise an organic polymer such as collagen, typically in combination with other ingredients as discussed below. In many embodiments the supports are porous. The support may be provided or mounted on a porous carrier (e.g., a porous membrane, a mesh, an inorganic grid, a hydrogel, or a combination thereof) to lend structural support thereto, as also discussed below. The support may be in any suitable shape or configuration, including flat, tubular, curved, spherical, ellipsoid, etc., including composites there (e.g., to emulate macroanatomical structures).

Supports with wells to facilitate the formation of lumens or crypts. In some embodiments the support top surface has a plurality of wells formed therein. Each of the wells having a top opening, side walls and a floor (and typically not extending entirely through the support). In these embodiments, the gastrointestinal epithelial cell monolayer extends into the wells—that is, onto the well side walls and (generally) floors, with the well top openings remaining open, to form open lumens (or "crypts") lined with cells in the wells.

In general, the wells are from 100, 200 or 300 microns deep, up to 800 or 1000 microns deep or more, and/or the wells are from 10 or 50 microns wide, up to 100 or 200 microns wide or more; and/or at least 10, 50, or 100 of the wells are formed in the top surface. Any suitable number of wells may be formed on the top surface, but in some embodiments at least 10 or 100 wells are formed, up to 1,000 or 10,000 or more, depending upon the particular use of the construct.

The wells may have any suitable geometry, including a square, rectangular, circular, or elliptical profile, or other composite thereof; may have vertical or sloped side walls, or a combination thereof; may have flat or rounded floors, or a combination thereof; etc.

With constructs such as described above, a gradient of the stem cells (and/or the differentiated cells, or types of differentiated stem cells) may be formed in the monolayer. This can be achieved by: (a) providing a construct as described above; (b) contacting a first culture media to the construct top surface; and (c) contacting a second culture media (different from the first culture media) to the construct bottom surface. One of the culture media induces the differentiation of propagating stem and progenitor cells and the other of the culture media induces the propagation of undifferentiated cells (e.g., by inclusion of appropriate signaling factors, as discussed further below). The gradient will typically be oriented or aligned with the well walls (e.g., with the ratio of stem cells to differentiated cells being greater at the bottom of the well than at the top, or vice versa), as discussed further below.

Other support materials. Besides collagen, other types of ECM's can be used to build a biomimetic scaffold. These include, but are not limited to, gelatin, laminin, elastin, fibronectin, heparin sulfate, chondroitin sulfate, keratin sulfate, hyaluronic acid, gelatinous protein mixture secreted by Engelbreth-Holm-Swarm mouse sarcoma cells (e.g. Matrigel®, Geltrex®, MaxGel™, etc.), and a mixture of the above ECMs (e.g. a collagen/Matrigel mixture). Hydrogel from natural polymers and synthetic polymers can also be used to build this scaffold, followed by surface engineering the scaffold with ECM molecules. Examples of natural polymers and synthetic polymers include chitosan, agarose, alginate, polyvinyl alcohol, sodium polyacrylate, acrylate polymers, polyethylene glycol, synthetic peptides, etc.

As noted above, the supports may also be inorganic, or a composite of organic and inorganic materials. Examples of inorganic materials suitable for supports include, but are not limited to, glass, hydroxyapatite, Bioglass such as 45S5 Bioglass, calcium phosphate, silicon, silicon oxide, titanium oxide, gold, aluminum oxide, etc. Where not inherently porous, these materials can be made porous by a variety of methods, including but not limited to sintering, etching, leaching, lithography, etc. For example, a porous mesh of silicon and gold can be fabricated by lithography/etching.

The supports or scaffolds can mimic or substantially mimic the biophysical microenvironment (lamina propria) in terms of the permeability, stiffness, and presence of ECM components. The scaffolds can be fabricated from polymer hydrogel contains 51-100 wt % water and 0-49 wt % polymer. The polymer includes natural polymers (e.g. collagen, gelatin, Matrigel, laminin, chitosan, agarose, etc.) and synthetic polymers (polyethylene glycol, polyvinyl alcohol, etc.) The scaffolds can be fabricated from non-hydrogel materials that are tailored to have a layer of ECM proteins on their surface. The scaffolds can be porous or permeable to allow the passage of nutrients, factors, metabolites and other molecules. By virtue of this permeability, the tissue grown on such scaffolds can be subjected to gradients orthogonal to the plane of the tissue. Gradients can also be formed parallel to the surface of the tissue i.e. across the tissue surface. Perpendicular gradients across the 3D scaffolds maintain both stem cell and differentiated cells on the same scaffold by application of a gradient of growth factor across the scaffold. The scaffolds can be biodegradable to allow implantation for regenerative medicine applications. The scaffolds can be attached to a solid surface, or free-standing. The scaffold can be mixed with cellular materials (cells, tissues, blood, microbiota), or non-cellular materials (drugs, polymer beads, magnetic particles, etc.) Addition of sodium butyrate to the medium enhances the culture of colonic epithelial cells on the scaffolds. The tissue is long-lived as the stem cells provide the source for self-renewal. The 3D scaffolds contain microstructures (e.g. microwells, microposts, channels, stripes and other microstructures). The methods can be extended beyond colonic epithelium to other healthy gastrointestinal (GI) epithelial tissues (including small intestine, stomach, esophagus, tongue, pancreas, etc.), and non-GI tissues possessing stem cells (liver, brain, hair follicle, kidney, retinal epithelium, etc.), as well as the diseased tissues.

Other factors, chemicals and drugs that can be used to form or impact crypts in vitro or alter their function. Gradients in signaling of factors (Wnt, BMP [bone morphogenic protein], and Notch) are thought to participate in crypt polarity by regulating cell position and proliferation. Besides the gradient of Wnt-3A proteins described above, other factors, small molecules and drugs can be used to regulate the cell signaling pathways to induce the polarization of tissues. The factors, small molecules and drugs include activators and inhibitors of Wnt, BMP, GREM1,2, Notch signaling pathways. Examples are CHIR99021 (Wnt activator), IWP (Wnt inhibitor), Y-27632 (Notch inhibitor), Noggin (BMP inhibitor), Jagged 1 (Notch activator), Gremlin (BMP antagonist), cytokines, dietary compounds (fiber, butyrate, other fatty acids, metabolites), etc. Other fatty acids include propionate and acetate, which are short-chain fatty acids produced by microbial fermentation of fiber, and additional metabolites include branched chain fatty acids, bile acids and microbial-derived secondary bile acids, urea, amines, ammonia, lactate, phenols, indoles, sulfurs, carbon dioxide, hydrogen, hydrogen sulfide, and methane. Metabolites include those from complex carbohydrates (soluble fiber), beans, and resistant starches, and can be produced from microbiota. Other chemicals include antidiuretic hormone, laxatives, bacterial endotoxins, hormones (e.g., VIP), and endogenous substances (e.g., bile acids), aldosterone, somatostatin, alpha2-adrenergic agents (e.g., clonidine), acetylcholine, nitric oxide, adenosine triphosphate (ATP), etc.

Other membranes can be used beneath the biomimetic scaffold. The biomimetic scaffolds can be fabricated on a support as described above. The supports include porous membrane (polytetrafluoroethylene [PTFE], polyester, polycarbonate, and cellulose), meshes (nylon, biodegradable polymers, metal), inorganic grit materials, hydrogels, and others.

Other scaffolds can be used to support the long-term proliferative activity and viability of intestinal epithelial cells in the 2D monolayer. The scaffolds can mimic the biophysical microenvironment (lamina propria) in terms of the permeability, stiffness, and presence of ECM components. The scaffolds can be fabricated from polymer hydrogel that contains 51-100 wt % water and 0-49 wt % polymer. The polymer includes natural polymers (e.g. collagen, gelatin, Matrigel, laminin, chitosan, agarose, etc.) and synthetic polymers (polyethylene glycol, polyvinyl alcohol, etc.) The scaffolds can be fabricated from non-hydrogel materials that are tailored to have a layer of ECM proteins on their surface. The scaffolds are in many cases porous or permeable to allow the passage of nutrients, factors, metabolites and other molecules. The scaffolds can be biodegradable to allow implantation in bodies. The scaffolds can be attached to a solid surface, or freestanding. The scaffold can be mixed with cellular materials (immune cells or other cell types, tissues, blood), or non-cellular materials (drugs, polymer beads, magnetic particles, etc.) Addition of a short-chain (e.g., C1 to C4 or C6) fatty acid such as sodium butyrate to the medium enhances the culture of colonic epithelial cells on the scaffolds. 3D scaffolds can maintain both the stem cell and differentiated cells on the same scaffold by applying a gradient of growth factor across the scaffold. The tissue is long-lived as the stem cells provide the source for self-renewal. The 3D scaffolds contain microstructures (e.g. microwells, microposts, channels, stripes and other microstructures). The methods can be extended beyond colonic epithelium to other healthy gastrointestinal (GI) epithelial tissues (including small intestine, stomach, esophagus, tongue, etc.), and non-GI tissues possessing stem cells (liver, brain, hair follicle, kidney, retinal epithelium, etc.), as well as the diseased tissues.

3. Utilities.

The current in vitro models for most epithelial tissues still rely on the use of immortalized cell lines derived from tumors. For example, Caco-2 cells derived from a colon carcinoma are widely used in mimicking the intestinal epithelium.[26-28] Although these tumor cell lines can form a contiguous monolayer, their cancer phenotype poorly reflects normal tissue physiology or microarchitecture found in vivo. This issue points to one of the major challenges of an in vitro tissue model which is the use of primary cells derived from normal tissue to form systems more representative of in vivo organ systems.[29] The 3D organoid culture systems overcame this need for continual culture of cells derived from primary cells, but remain limited by the enclosed architecture of the spheroidal organoid and need to culture within a gelatinous layer as opposed to a standard open surface typical of traditional tissue culture systems (for example, this may be be contrasted to Calvin Kuo's air-liquid interface cultures. These are comprised on all layers (ie. Epithelium and mesenchyme) that are grown on flat surfaces and have a polarized epithelium and an exposed luminal surface. The difference again is that they are not long-lived and growth and differentiation is random and uncontrolled to a certain extent.). This surface may be planar or convoluted but is characterized by having an open architecture unlike the organoids which are closed structures. By inventing a culture system characterized by an open architecture, this work has overcome the limitations of the organoid system making the culture of epithelial tissues composed of primary cells compatible with conventional tissue culture methods and current robotics used in automated, high-throughput culture and analysis platforms. The open architecture and permeable substrate make possible culture of cells under gradients of soluble factors both parallel and orthogonal to the epithelial surface. The open architecture will enable assays of epithelial barrier function, absorption, and secretion not possible in enclosed systems. Interactions of the primary epithelium with overlying bacteria and other components of a microbiome are also now possible. These ex vivo tissues can be created from a variety of species including mouse, pig, and human among others. Model systems developed from transgenic animals, genetically modified human stem cells (e.g. TALEN or CRISPR/cas), induced pluripotent stem cells and stem cells derived from animal and human organisms with particular diseases are other non-limiting examples of materials that can be used to create these tissues. The ability to create these tissues from healthy and diseased sources and from cells of differing genetic backgrounds will be important for screening drugs, study of disease mechanisms, and study of basic biology. Addition of various other cell types (e.g. immune cells, fibroblasts, and others found co-existing with the particular epithelial tissue in vivo) co-cultured on or within the biomimetic scaffold will be valuable for understanding cell-cell interactions and the effect of drugs and metabolites on the tissue. We posit that the epithelial tissues generated on the biomimetic scaffolds using primary tissue are superior to the current cell models for study of epithelial tissues. Some examples follow but this list is not all inclusive.

1) In vitro model for physiologic studies (molecular transportation across the intestinal epithelial cells, induced enzymatic functions, interaction with bacteria)
2) Screening studies of drugs, biologics, toxins, mutagens, dietary compounds, pathogens, viruses, microbiota, etc.
3) Screening studies of microbiota under controlled conditions (oxygen tension, drug exposure, dietary compounds, metabolites, etc.)
4) Disease models by using stem and primary cells derived from a translational animal models or human
5) Pharmacological and pharmacokinetic models for screening including comprehensive dose-response profiles for drugs, dietary compounds, etc.
6) In vitro models to study metabolism
7) In vitro models for wound healing of epithelial tissue to maintain barrier function
8) In vitro models for study bacteria-epithelium interaction
9) Tissue engineering for implantation to repair damaged epithelium
10) Personalized medicine by studies performed on specific genetic backgrounds and individual patients
11) Performance of assays such as: absorption of water and electrolytes (sodium, chloride, protons, bicarbonate, potassium), and the salvage of unabsorbed nutrients
12) Impact of mucous flow, movement, and production as well as diseases stemming from this such as in cystic fibrosis
13) Assays of antidiarrheal agent
14) s, opiates, and treatments for constipation, for example, laxatives
15) Assays of syn-, pre- and probiotic agents.
16) Assay of radiopaque and scintigraphic markers and their impact on epithelium
17) Impact of immune cells and their products (antibodies and cytokines) on epithelium
18) Assay of soluble and insoluble fiber and its impact on the epithelium
19) Understanding response to and repair of epithelium in response to injury of any type
20) Investigation of bacteria leading to pseudomembrane formation, for example, *Clostridium difficile*
21) Screening for carcinogenic compounds
22) Screening for biowarfare compounds
23) Studies to prevent GI bleeding as a side effect of NSAID treatment.
24) Studies of the role of the immune system on epithelial integrity and disease (e.g. inflammatory bowel diseases, enteropathies, cancer, etc.).
25) Assays for radio-and chemotherapeutics and agents that ameliorate off-target effects.
26) Ex vivo tissue expansion.

While the above applications relate primarily to studies enabled by the planar in vitro tissue constructs, the constructs can be envisioned as a means to create new tissue for repair of damaged or diseased tissue in the body. For example, the 2D monolayer could be used for regenerative medicine as follows: stem cells could be obtained from biopsy of a patient with digestive epithelial damage (e.g. from inflammatory bowel disease). The stem cells could be expanded on the scaffold to generate a large number of proliferative cells. The cells can be detached from the culture vessel, and placed back to the same patient to repair the damaged epithelial tissue.

4. Screening Methods.

Thus, as noted above, in some embodiments the present invention provides a method of screening a test compound or microbe for a toxicological, physiological, or carcinogenic effect, comprising: (a) providing a construct as described above; (b) contacting a test compound or microbe to said construct; and then (c) detecting a toxicological, physiological, or carcinogenic effect of said microbe on the cells of said construct (e.g., by comparing the construct after said contacting to a like construct to which said compound or microbe has not been contacted, and/or by comparing the construct after said contacting step to said construct before said contacting step).

In some embodiments, the test compound or microbe is selected from the group consisting of aromatic organic compounds, aliphatic organic compounds, and mixed aromatic and aliphatic organic compounds. For example, in some embodiments, the compounds for screening are compounds are natural products, prebiotics, probiotics, foodstuffs, carcinogens, drugs, drug metabolites, bacterial metabolites and toxins, irritants, soil compounds, ingestible toxins, etc.

In some embodiments, the test compound or microbe is selected from the group consisting of gram negative bacteria, gram positive bacteria, yeast, and molds. For example, In some embodiments, the microbe is a bacteria of a type found in the ordinary or healthy gut flora (or "microbiome") of mammalian, particularly human, species. See, e.g., US Patent Application Publication No. US 20140093478. In some embodiments, the microbe is an infectious organism, such as clostridium, cholera, salmonella, shigella, worms (tape, pin, hook, eyc), amoeba (giardia, etc), etc. Thus in some embodiments, the microbe is an enteric bacteria or pathogen, including both benign and infectious enteric bacteria and pathogens.

Suitable detection methods include, but are not limited to, immunohistochemistry, PCR for DNA, mRNA expression, RNA sequencing, transepithelial electrical resistance, transport assays (ion, compound, protein, etc.), secretion assays, electron microscopy, flow cytometry, mass spectrometry of supernatants or reservoirs, ELISA and radiochemistry assays of the same, fluorescence based sensors of the same, and microbe adhesion to the epithelial cells.

The present invention is explained in greater detail in the following non-limiting examples. While particular examples of colonic monolayers are given, it will be appreciated that monolayers from other gastrointestinal epithelial cells can also be formed, particularly small intestine, intestine, stomach, esophagus, tongue, nasopharynx, oropharynx, laryngeopharynx, and pancreatic epithelial cells, etc., in like manner as described below or by variations of such techniques that will be apparent to those skilled in the art.

EXAMPLE 1

Demonstration of Long-Term Colonic Epithelial Monolayers on both 2d and 3d Scaffolds As a demonstration of the current invention, two types of scaffolds, 2D and 3D scaffolds, were fabricated from collagen and demonstrated to support the long-term culture of cells obtained from primary colonic crypt tissue including the stem cells (FIG. 1). A 2D colonic epithelial monolayer was generated by culturing isolated crypts or stem cells on the surface of the planar, 2D scaffolds (FIG. 1A). Under this condition, the biochemical microenvironment was provided by the soluble growth factors (Wnt-3A, R-spondin, noggin and EGF), while the biophysical microenvironment was provided by the collagen scaffold which mimics the lamina propria in terms of permeability, stiffness, and ECM components. The monolayer contained proliferative stem cells. By changing the growth factors in the medium, the monolayer could be selectively differentiated at will into specialized cells, such as goblet cells and enterocytes (FIG. 1A).

To more closely recapitulate the in vivo biophysical/biochemical microenvironment of crypts, a 3D scaffold was used that possessed an array of microwells and a gradient to guide the generation of colonic epithelium with a polarized architecture (i.e. distinct proliferative and non-proliferative zones or stem-cell and differentiated-cell compartments), and a geometry that more closely resembled the colonic epithelium in vivo than the 2D scaffold (FIG. 1B). However, other shapes to the underlying scaffold are also possible, for example, one with the shape of the villi and crypts of the small intestine, the papillae and taste buds of the tongue, glands and the gastric pits of the stomach. An open-lumen crypt was generated on the 3D scaffold by continual culture of cells derived from crypts or purified stem cells on its surface. The tissue recapitulated the overall mushroom-shaped geometry of colonic crypts. Additionally, by applying a gradient of soluble growth factors across the scaffolds, the tissue was shown to be polarized into distinct proliferative and non-proliferative zones to mimic that present in vivo (FIG. 1B). Therefore, in vitro crypts were created that mimicked all characteristics of in vivo crypts: (1) luminal and basal sides, (2) open lumen, (3) stem cell and proliferative cell compartments at basal side, and (4) proliferating cells migrating from the basal side towards the lumen forming differentiated cells. The overall surface could be planar or nonplanar.

Figure 2:
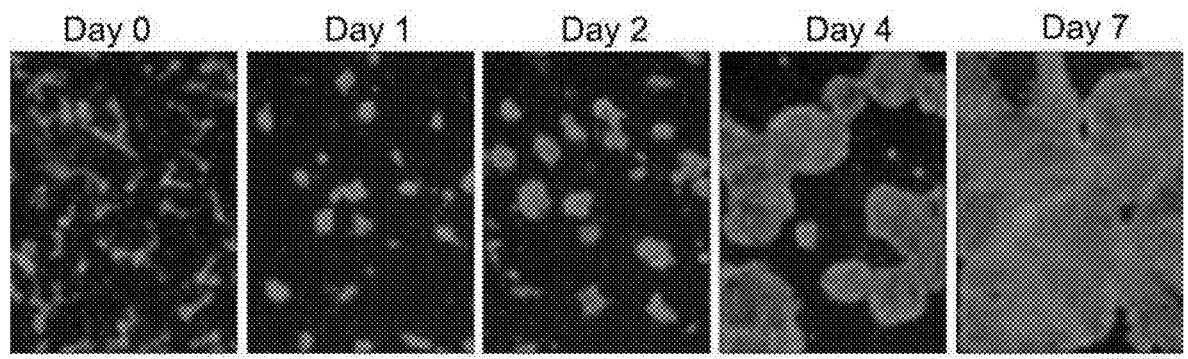
FIG. 2. 2D culture of crypts on a collagen hydrogel scaffold surface. The cells were proliferative on the surface at day 7 to form a contiguous layer. Scale bars=500 µm.

Results 2D culture of crypts on biomimetic scaffolds produced a proliferative, long-lived 2D monolayer._A biomimetic, planar scaffold was fabricated from collagen (rat tail, type I, 2 mg/mL) by adding 1 mL neutralized collagen precursor to one well of a 6-well plate and polymerized at 37° C. for 30 minutes. The scaffold mimicked the loose connective tissue of the lamina propria as it contained 99.8 wt % water and 0.2 wt % collagen protein. A CAG-DsRed mouse model whose cells express the DsRed fluorescent protein was used to monitor the proliferation of colonic epithelial cells by fluorescence microscopy. 2D culture of crypts on the scaffold was performed in a similar manner to standard 2D cell culture (FIG. 2). The colonic crypts were plated on the scaffold and cultured in a medium containing Wnt-3A, R-spondin, Noggin, and EGF. Sodium butyrate (0.5 mM) was added in the medium. Butyrate is a dietary factor produced locally in the colon by anaerobic bacterial fermentation of dietary fiber. Butyrate is a short-chain fatty acid that serves as the primary energy source for colonocytes, and a previous study has shown that without butyrate for energy, colonic cells undergo autophagy.[21] Besides being an energy source, sodium butyrate has been shown to act in other roles such as an HDAC inhibitor[22] and notch activator.[23] The culture medium used for these experiments is termed ENR-WB (E-EGF, N-noggin, R-spondin, W-Wnt-3A, B-butyrate).

Figure 3:
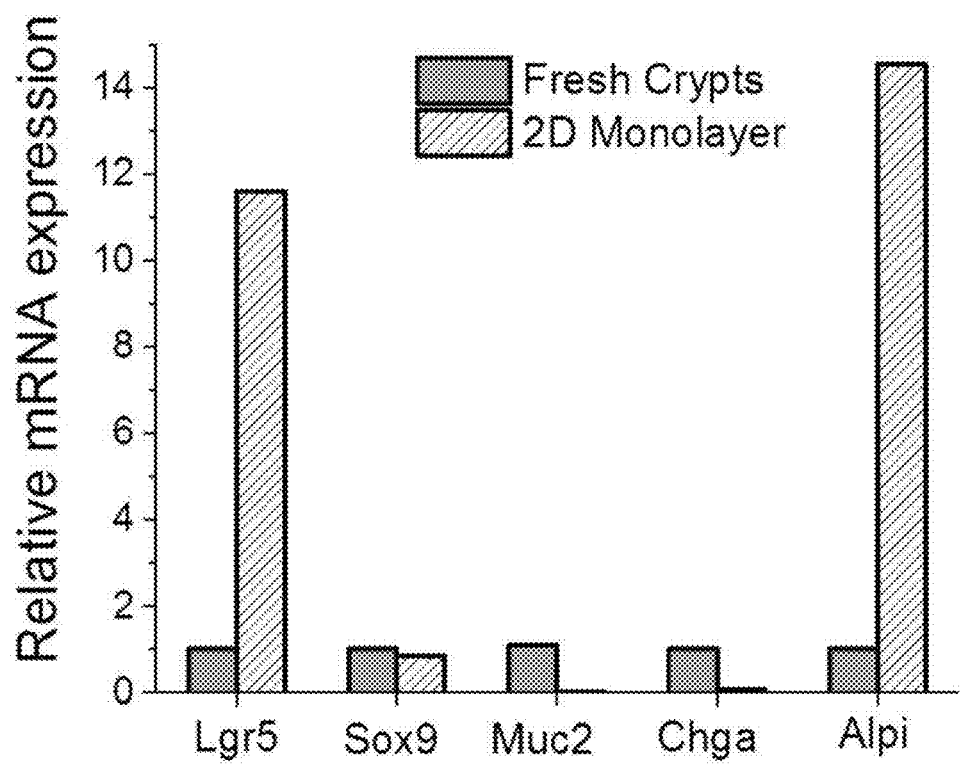
FIG. 3. Relative messenger RNA expression of stem cell marker (Lgr5), stem/progenitor cell marker (Sox9), mature epithelial cell markers (Alpi, Chga, muc2) for 2D monolayer cultured under ENR-WB for 7 days. Freshly isolated colon crypts were used for control. Data are average of two samples for fresh crypts and 2D monolayer.

Isolated crypts were loaded on the scaffold where their cells adhered to the scaffold surface within a few hours. By 24 h, crypts placed on the scaffold surface formed small patches of cells in a 2D, densely packed monolayer (FIG. 3). The patches of cells continued to spread until an almost contiguous monolayer of cells was formed at day 7. Cell apoptosis, an indication of cell differentiation, was not observed at this relatively early time point. This result demonstrated that the collagen scaffold provided the necessary biophysical signals to the stem cells to maintain their proliferation capability as is shown in data described below. It also showed that cell/crypt encapsulation within an ECM gel was not required to maintain stem cell activity. The monolayers were long-lived, for at least 20 days, the longest time tested.

Stem/progenitor cells make up the 2D monolayer on scaffolds._The 2D monolayer on a collagen scaffold is composed of a mixture of stem/progenitor cells and differentiated cells, rather than being comprised of only differentiated cells. This statement is supported by the following experimental evidence.

(1) The cells in the monolayer were analyzed by reverse-transcriptase polymerase chain reaction (RT-PCR). The RT-PCR result (FIG. 3) showed that the expression of the stem cell marker gene Lgr5 was substantially elevated for the 2D monolayer compared with freshly isolated crypts. The differentiation marker genes Muc2 and Chga were down regulated relative to that found in fresh crypts. The stem/progenitor marker gene of Sox9 did not differ from that found in fresh crypts. The enterocyte marker gene Alpi was substantially upregulated, although the monolayer was negative for alkaline phosphatase (alp) colorimetric staining (FIG. 5A). Based on these results, the monolayer was likely composed of stem cells, progenitor cells and differentiated cells.

Figure 4:
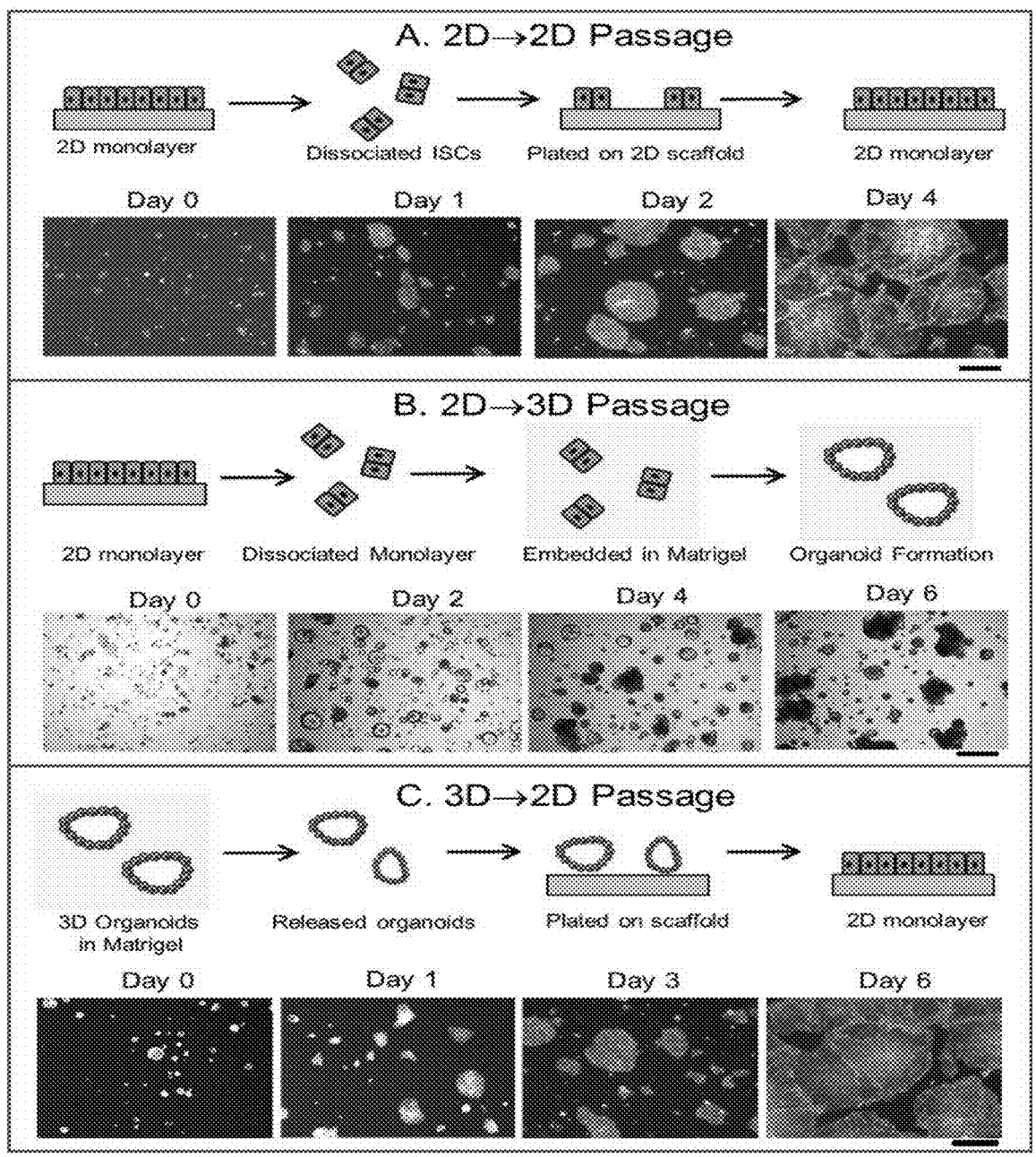
FIG. 4. Passage of 2D monolayer and switch between 2D monolayer and 3D organoids. (A) 2D→2D passage. (B) 2D→3D passage. (C) 3D→2D passage Scale bars=500 µm.

(2) The monolayers could be passaged multiple times in 2D format without losing the proliferative capability (up to 6 passages have been tested to date) (FIG. 4A). The 2D monolayer was detached from collagen scaffold by dissolving the scaffold with collagenase (type VI, 500 U/mL, 10 minutes). The cell layer was dissociated into small fragments by pipetting up and down. The cell fragments were re-plated on a collagen scaffold and cultured under the ENR-WB condition. The cell fragments attached to the new scaffold and grew into a proliferative monolayer again. This result demonstrates that the monolayers are made from both proliferative cells and differentiated cells (enterocytes, goblet cells) since only the proliferative cells retain the competency to recapitulate the monolayer. As noted above, those skilled in the art will appreciate that similar results can be obtained with other cells, such as small intestine cells, and with other differentiated cells (e.g., Paneth cells, enteroendocrine cells, tuft cells, microcells, intra-epithelial lymphocytes, etc., as well as enterocytes and goblet cells).

(3) The 2D monolayers can be converted to 3D organoids. The 3D organoid model is well-established for sustaining the proliferation of colonic stem cells. To prove that the monolayer possessed stem cells, we detached the 2D monolayer from the collagen scaffold and dissociated it into small fragments by repetitive pipetting. The cell fragments were embedded in Matrigel for 3D culture (FIG. 4B). The cell fragments grew into 3D organoids at day 2 and continued to expand into large organoids at day 6. In addition, the cells in the 3D organoids so prepared could be switched back to grow as a 2D monolayer by releasing organoids from Matrigel by repetitive mechanical pipetting, and plating the organoids on the collagen scaffold (FIG. 4C). The organoids spread on the scaffold at day 1 and formed a 2D monolayer at day 6 (FIG. 4C). These results demonstrate that the 2D monolayers and 3D organoids can be interconverted, supporting that both formats possess proliferative stem/progenitor cells as well as differentiated cells.

Figure 5:
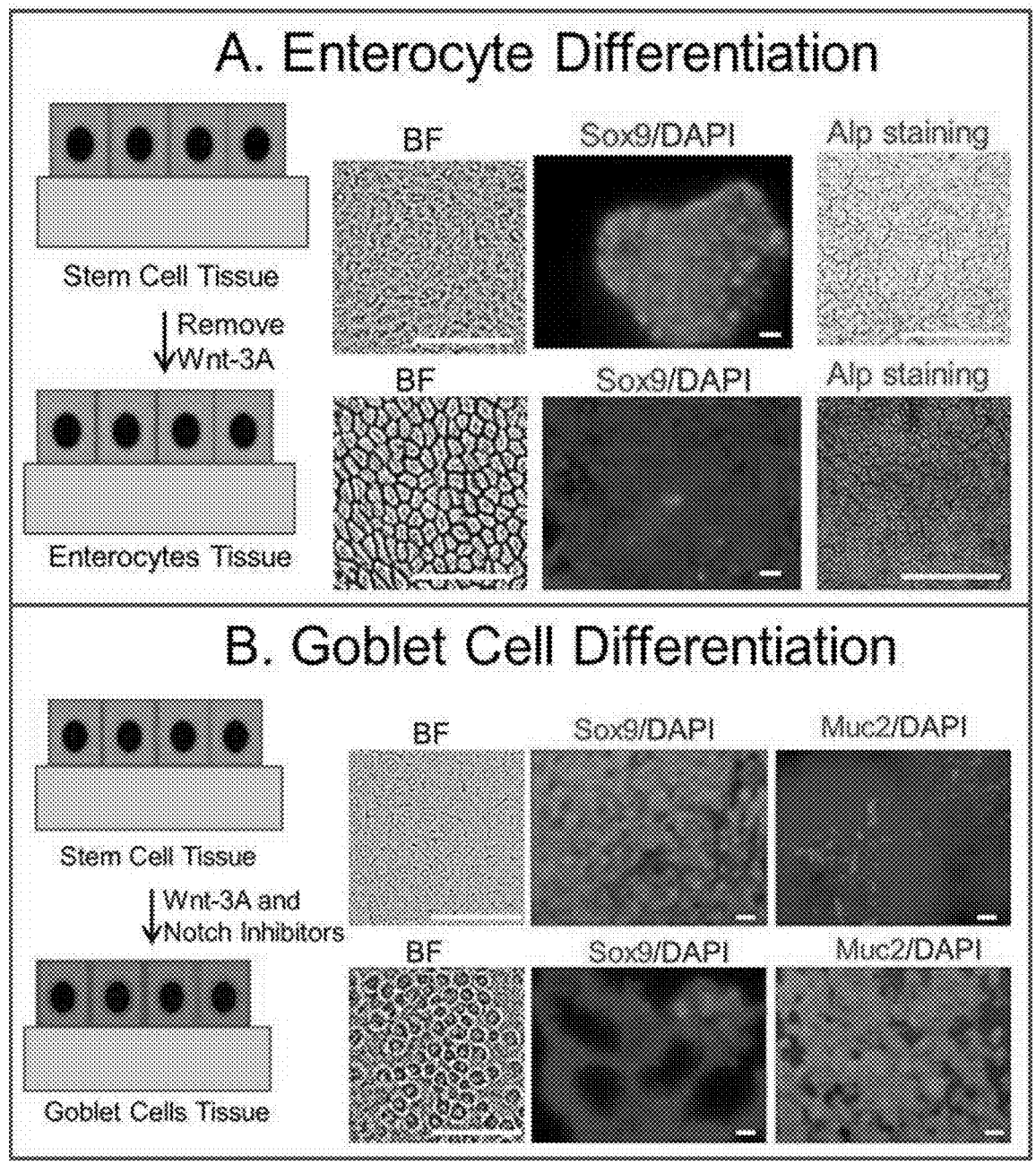
FIG. 5. Differentiation of 2D monolayer to specialized cells. (A) Enterocyte differentiation by removing Wnt-3A from the culture medium. The presence of enterocytes was confirmed by Alp staining. (B) Goblet cell differentiation by adding Wnt-3A and Notch inhibitors to the culture medium. The presence of goblet cells was confirmed by Muc2 staining. The loss of stem/progenitor cells was configured by Sox9 staining Scale bars=50 µm.

(4) Immunofluorescence staining shows the 2D monolayer cells are positive for staining with an antibody against Sox9 (FIG. 5). Antibodies against Sox9 are known to stain stem/progenitor cells but not differentiated cells. In addition, the monolayers do not show substantial fluorescence when stained for differentiated-cell staining markers (FIG. 5), i.e. alkaline phosphatase (alp), colorimetric staining (for enterocytes), and Muc2 (for goblet cells).

(5) The 2D monolayer can be selectively and fully differentiated into mature enterocyte and goblet cells (see next section for details).

The above results prove that the 2D monolayer on collagen scaffolds cultured under ENR-WB condition possesses stem/progenitor cells and is therefore self-renewing. It is the stem/progenitor cells that fuel the proliferation of the 2D monolayer.

A 2D monolayer on biomimetic scaffolds can be differentiated to short-lived, specialized cells. The in vivo colonic epithelium is composed of not only stem/progenitor cells, but also differentiated, specialized cells: enterocytes, goblet cells, and enteroendocrine cells. The function of stem/progenitor cells is to provide the source for the self-renewal of short-lived specialized cells. The functions of specialized cells range from absorption (enterocytes), mucus secretion (goblet cells), and hormone production (enteroendocrine cells). It is highly desirable to generate specialized cells for in vitro functional studies of colon epithelial physiology.

Similar to 3D organoids,[24] the stem/progenitor cells in the 2D monolayer are thought to be maintained by the activation of both Wnt and Notch signaling. Under ENR-WB conditions, Wnt-3A and R-spondin (Wnt signaling enhancer) act as Wnt signaling activators, while 0.5 mM sodium butyrate may act as the activator for Notch signaling.[23] To induce differentiation towards the enterocyte lineage, we first cultured the 2D monolayer on the collagen scaffold under ENR-WB for 4 days, and then treated the cells with enterocyte differentiation medium for 4 days. The enterocyte differentiation medium, ENR-B, does not contain Wnt-3A. The 2D monolayers before and after the treatment were inspected by brightfield imaging, Sox9/DAPI staining, and alkaline phosphatase (Alp) staining (FIG. 5A). After treatment, the cells became columnar epithelial cells with distinct cell boundaries (brightfield images). The cells lost Sox9 expression, but gained Alp staining. These results indicate that cells of the 2D monolayer were differentiated to enterocyte cells.

Inactivation of both Wnt and Notch signaling enabled differentiation towards goblet cell lineage in the 3D organoid culture model.[24] To test this in the 2D culture model, we first cultured the 2D monolayer on the collagen scaffold under ENR-WB for 4 days, and then treated the cells with the goblet differentiation medium for 4 days. The goblet differentiation medium does not contain Wnt-3A or butyrate, but contains Wnt inhibitor (2 µM IWP-2) and Notch inhibitor (10 µM LY-411575). The 2D monolayers before and after the treatment were inspected by brightfield imaging, Sox9/DAPI staining, and Muc2 staining (FIG. 5B). Secretory granules appeared (brightfield images) after treatment. The cells lost Sox9 expression, but gained Muc2 staining. These results indicate that 2D monolayer cells were differentiated to goblet cells.

Similar to what happens in vivo, differentiated cells (enterocytes and goblet cells) in the 2D monolayer are short-lived dying within a matter of a few days. The cells in the 2D monolayer started to die at around day 3 after treatment with differentiation medium, and all of the cells were dead and detached from the surface at day 6. Therefore, there is only a short window (2-3 days) to allow functional assay of these differentiated cells.

Generating 3D epithelial tissue constructs on 3D collagen scaffold using regenerating epithelial cell monolayers. The 2D monolayer on the planar scaffolds shown in FIG. 5 can be maintained as a cell layer possessing stem/progenitor cells under the ENR-WB condition, or induced to fully differentiate (enterocytes, goblet cells) when exposed to the differentiation medium. If a non-planar scaffold is used, such as the 3D scaffold possessing deep microwell structures shown in FIG. 1B, both stem/progenitor cells and differentiated cells (enterocytes, goblet cells) will exist but in distinct compartments on the same scaffold when a gradient of soluble growth factor of Wnt-3A with higher concentrations of this growth factor near the base of the microwell and lower concentrations near the top of the well and upper surface of the array. The stem/progenitor cells are located at the base of the microwells due to the presence of Wnt-3A, and the cells at the opening of the microwells differentiate to enterocytes due to the absence of Wnt-3A protein further from the source. A 3D scaffold and Wnt-3A gradient accurately recapitulate the in vivo biophysical/biochemical microenvironment of crypts. The generated 3D colonic epithelial tissue has a polarized architecture (i.e. distinct proliferative and non-proliferative zones), and open lumen, and a mushroom-shaped geometry that identifies the structure as a crypt.

Figure 6:
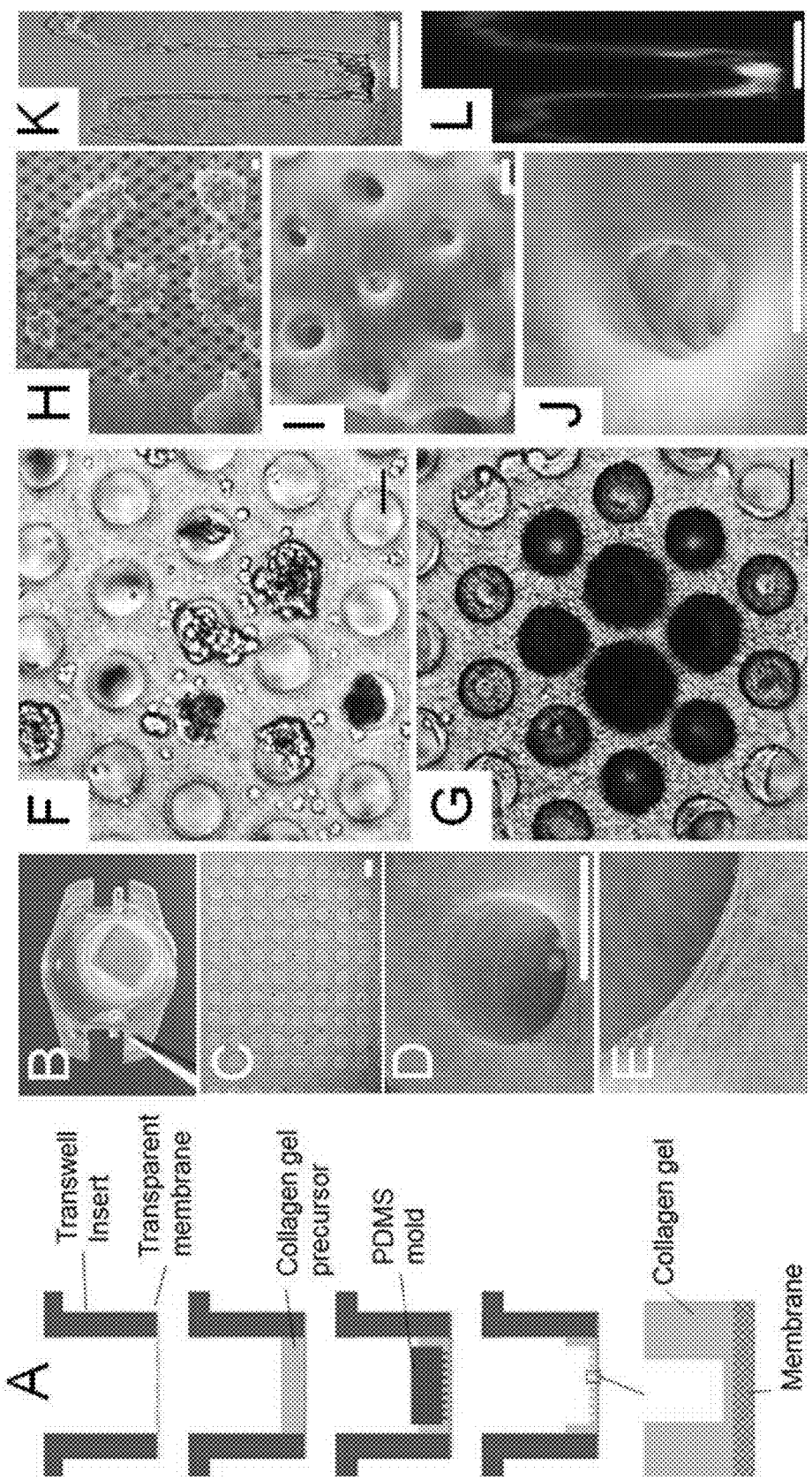
FIG. 6. 3D mushroom-shaped colonic epithelial tissue generated on 3D collagen scaffolds. (A) Schematics of fabrication of collagen scaffolds on a porous membrane by soft lithography molding process. (B) Photo of the device. The collagen microwell array is molded on a clear, porous PTFE membrane inside a Transwell insert. (C) BF image of the collagen scaffold. (D) SEM image of the scaffold. (E) Close image of red square in (D) shows the submicron collagen fibers. (F-G) Culture of colonic stem cells on the 3D scaffold. (F) Day 0. (G) Day 5. (H-J) SEM images of colonic epithelial tissues on the 3D scaffolds. (K-L) Microscopic images of sectioned scaffolds. (K) Brightfield image. (L) Fluorescence image. Blue=Hoechst 33342 nuclear staining. Green=Sox9EGFP. Scale bar=50 µm.

A 3D collagen scaffold was fabricated on a clear porous membrane using the process outlined in FIG. 6A. The clear porous membrane (hydrophilic PTFE, 0.4 µm pore size) was part of a plastic Transwell insert. 1 mL collagen solution (10 mg/mL in 0.02 M acetic acid) was neutralized with 0.325 mL neutralization buffer (a mixture of 1 part 10× PBS, 1 part 0.2 M sodium hydroxide, and 0.08 part 7.5 wt % sodium bicarbonate) and placed on ice. 0.25 mL collagen mixture was added on the porous membrane inside the Transwell insert. A PDMS mold possessing an array of microposts (post diameter=60 µm, height=240 µm, center-to-center gap=100 µm) was coated with 1 wt % bovine serum albumin, rinsed with water, and placed directly on the collagen. The insert was placed in a 4° C. refrigerator for 2 h, then moved to 37° C. and incubated for 1 h to polymerize the collagen. The PDMS mold was then slowly detached from the solidified collagen. An array of microwells (well diameter=60 µm, height=240 µm, center-to-center gap=100 µm) was created on the collagen scaffold on the top of the porous membrane. To increase the stability of the collagen scaffold, the scaffold was cross-linked for 4 hours at room temperature by 0.2 M 1-ethyl-3-(3-dimethylaminopropyl) carbodiimide (EDC) and 0.05 M N-hydroxysuccinimide (NHS) in 0.03 M 2-(N-morpholino)ethanesulfonic acid (MES, pH 5) buffer. The scaffold was then rinsed with water, sterilized with 75% ethanol, and finally rinsed with PBS buffer.

FIG. 6B shows a photo of the Transwell insert that contained the 3D collagen scaffold. The central square portion (6 mm×6 mm) contained 3,600 microwells. The insert is placed in the well of a 12-well plate. The clearance of the porous membrane and collagen scaffold allows imaging the scaffold by both brightfield and fluorescence microscopy. The brightfield image of the scaffold is shown in FIG. 6C. Scanning electron microscope (SEM) images in FIGS. 6D and 6E show the highly porous structure of the collagen scaffold prepared by critical point drying. The scaffold is intermingled with submicron collagen fibers (FIG. 6E).

Fragments of colonic epithelial cells were plated on the 3D scaffold. The fragments landed into microwells of the scaffold (FIG. 6F). At day 5 of culture, the cells formed a continuous tissue layer along the scaffold (FIG. 6G). Notably, the lumen of the tissue was open creating a structure with many crypt features in vitro as revealed by SEM images (FIG. 6H-J).

The tissue was polarized by culturing the cells under ENR-WB condition for 4 days, followed by a gradient of Wnt-3A for 3 days. We used colonic stem cells derived from the Sox9EGFP mouse model. Since EGFP was expressed under the Sox9 promoter and Sox9 expression is restricted to intestinal stem and progenitor cells (but not to the differentiated colonic epithelium),[25] EGFP was used as an indicator of proliferative cell capacity. To establish the gradient of Wnt-3A, 0.5 mL ENR-B medium was added in the upper compartment and 1.5 mL ENR-WB medium was added to the lower compartment. Media was changed daily. At the end of culture, the tissue was fixed with glutaraldehyde, stained with nuclear Hoechst 33342 dye, and cryo-sectioned. The tissue was 3D, and contained an open lumen and mushroom-shape, being consistent with SEM images (FIG. 6K). Notably, EGFP expression was found to be located at the basal aspect of the tissue, not at the luminal side, demonstrating polarization of the structure and formation of a true crypt with a distinct stem-cell and differentiated-cell compartment (FIG. 6L). Cell proliferation (EGFP$^+$) was maintained by the high Wnt-3A concentration at the basal side, while differentiation (EGFP$^-$) occurred at the luminal side where Wnt-3A concentration was low. These demonstrate formation of in vitro tissue possessing crypts on the microwell scaffold. The tissue demonstrated both the geometry, architecture and polarization of crypts in vivo. The biomimetic scaffolds enable forced localization of stem cells to the base of the synthetic crypts with subsequent natural gradient formation from endogenous release of mitogens/morphogens. Co-culture of biologically important support cells can be expanded ex vivo and the layered onto the biomimetic scaffolds to generate engineered intestinal/colonic tissue layers.

EXAMPLE 2

Figure 7:
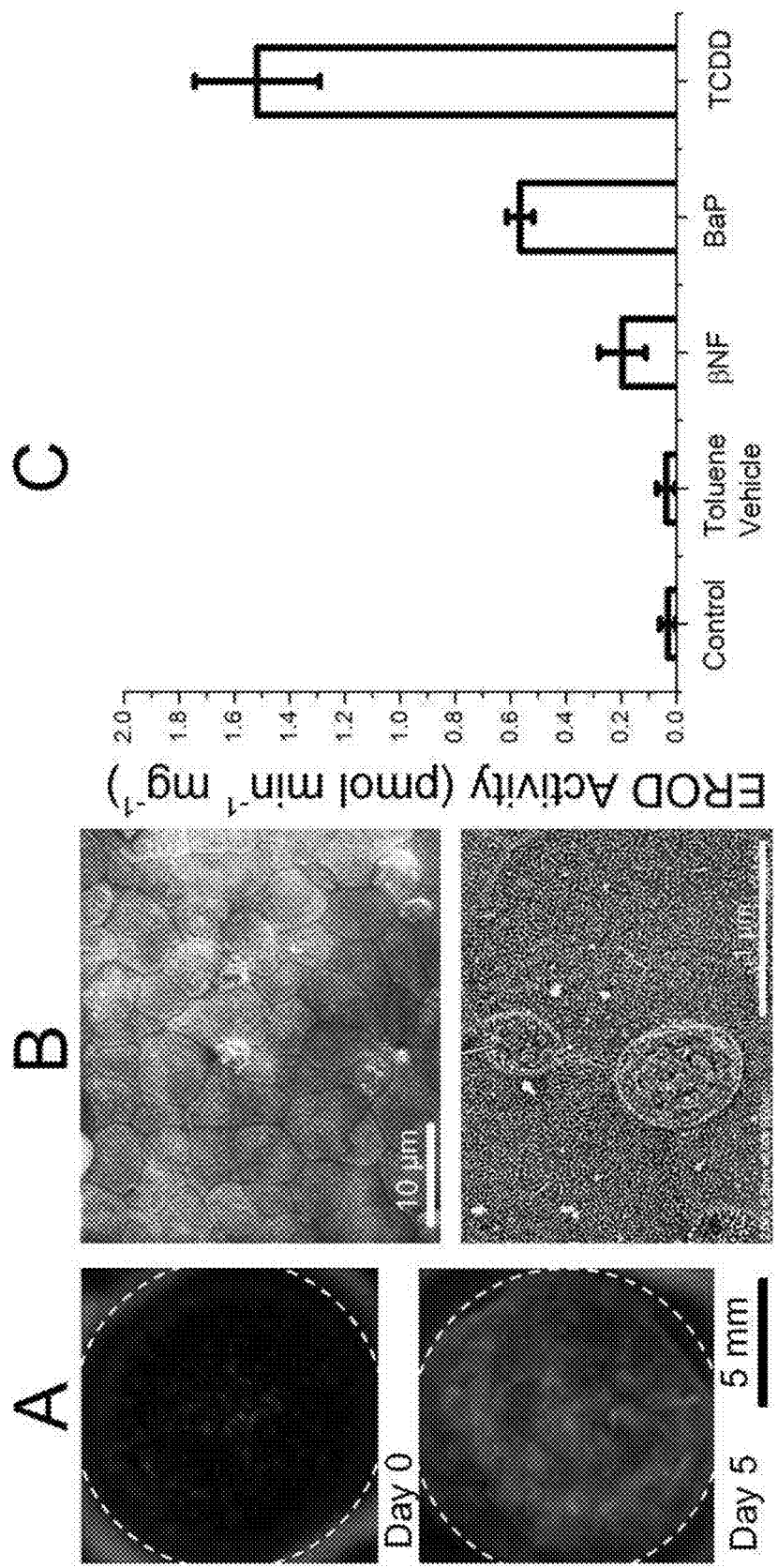
FIG. 7. In vivo-like proliferating capability, morphology and function of the 2D colonic epithelial monolayer. (A) A continuous 2D monolayer possessing an area of 137 $mm^2$ was generated in a Transwell insert at day 5. Top panel, day 0. Bottom panel, day 5. White dotted line indicates the perimeter of the insert. (B) SEM images of 2D monolayer. Arrows indicate secretory cells. (C) Basal EROD activity and inducibility in 2D monolayer cells. 2D monolayer was cultured under ENR-WB for 5 days. At day 5, the cells were treated with enzyme inducers (βNF, BaP and TCDD) for 20 hours. CYP1A1 enzyme activity was determined using the ethoxyresorufin O-deethylase (EROD) assay, n=3.

The 2d Monolayer Possesses In Vivo-Like Proliferating Capability, Morphology and Function In vivo, the intestinal epithelium is one of the most rapidly proliferating tissues in the mammalian body. Consistent with this, the in vitro 2D monolayer of colonic epithelial cells cultured on the collagen scaffold was highly proliferative. To demonstrate this proliferative capability, fragments of 2D monolayer were plated on the collagen scaffold in a Transwell insert (FIG. 7A, top panel). The perimeter of the insert is indicated by the white dotted line). By day 5, the cells generated a continuous 2D monolayer that occupied the entire surface of the insert with a surface area of 137 mm$^2$ (FIG. 7B, bottom panel). This result demonstrates that the 2D monolayer culture technique can generate a large piece of colonic epithelial tissue in vitro, which is impossible to accomplish with the 3D organoid culture technique.

To investigate if the in vitro tissue possesses in vivo-like morphology, the 2D monolayer cultured on collagen scaffold at day 5 was inspected by scanning electron microscope (SEM). The cells in the 2D monolayer displayed a cobblestone-like morphology and arrangement (FIG. 7B, top panel), a characteristic of intestinal epithelium found in vivo. Most cells possessed microvilli at their apical surface (FIG. 7B, bottom panel). Goblet cells were also present in the 2D monolayer (indicated by arrows in FIG. 7B), which possessed vesicles on their apical surface to release mucus. The SEM images show that the in vitro tissue (in this non-limiting example) possesses in vivo-like morphology.

Intestine is a vital organ that has many important functions (such as absorption, secretion, etc.). One function is metabolism through cytochrome P450 (CYP) enzyme activity that provides the principal, initial source of biotransformation/detoxification of ingested xenobiotics (Kaminsky, L. S. et al., *Critical Reviews in Toxicology* 21, 407-422 (1992)). Among the CYPs, CYP1A1 plays a physiological role in the degradation of estradiol into 2-OH-estradiol (Paine, M. F. et al., *Drug Metabolism and Disposition* 27, 360-364 (1999)). In vivo, CYP1A1 in rat intestines can be induced by feeding the rats with polycyclic aromatic hydrocarbons (PAHs) (Martignoni, M. et al., *Chemico-Biological Interactions* 151, 1-11 (2004)). To investigate if the in vitro 2D monolayer possesses this type of in vivo-like function, the 2D monolayer was treated with three types of PAHs (1000× dilution in medium, toluene was used as vehicle) for 20 hours: 10 μM beta-naphthoflavone (βNF), 1 μM benzo[a]pyrene (BaP), 0.1 μM 2,3,7,8-tetrachlorodibenzo-p-dioxin (TCDD). The CYP1A1 enzyme activity was determined using an ethoxy-resorufin O-deethylase (EROD) assay (Jones, S. P. et al., *Ecotoxicology* 23, 802-808 (2014)). The CYP1A1 enzyme activity was effectively demonstrated by all of three PAHs (FIG. 1C). TCDD is the most potent CYP1A1 inducer, with the CYP1A1 activity 40-fold increased compared with the cells treated with toluene vehicle. This result demonstrates that the 2D monolayer possesses an in vivo-like function: the ability to induce CYP1A1 activity.

EXAMPLE 3

Figure 8:
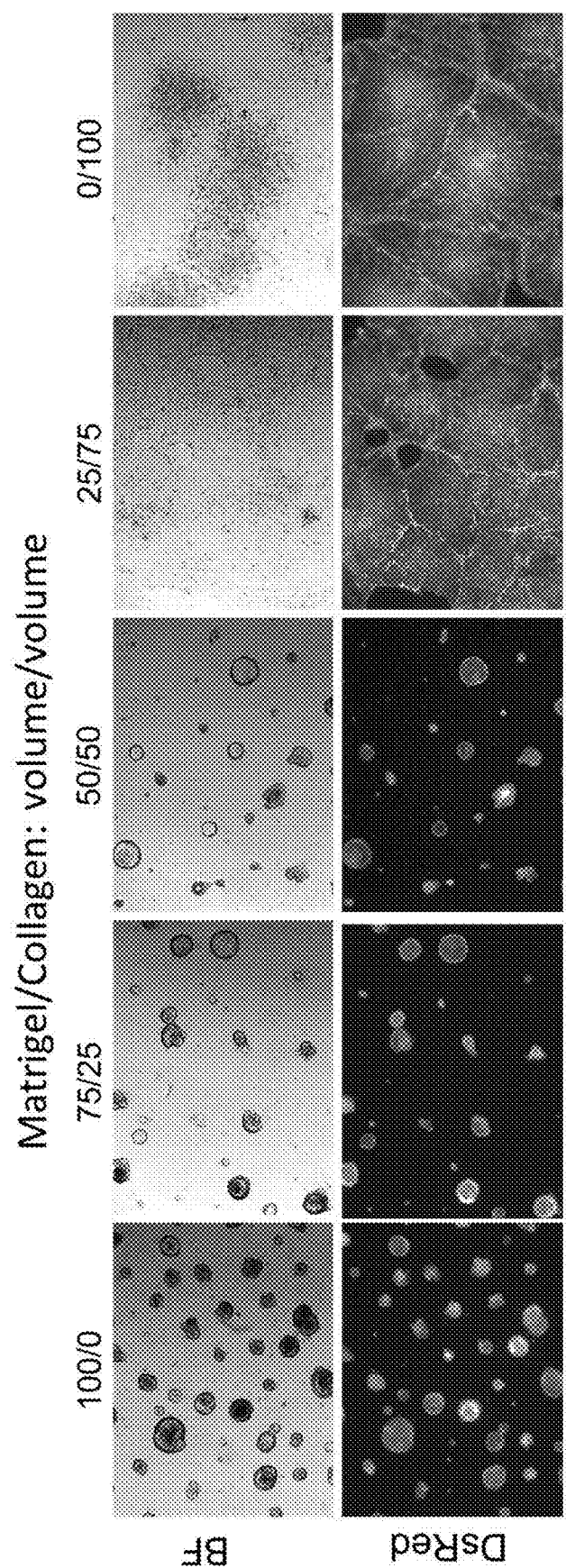
FIG. 8. Colonic epithelial cells cultured under ENR-WB for 5 days on Matrigel/collagen scaffold with a variety of mixing ratio. Top panel is brightfield image. Bottom panel is DsRed fluorescence image. Scale bar=1 mm.

Scaffold Composition and Properties Determine the Morphology of Colonic Epithelium We have shown that the colonic epithelial cells form a 2D monolayer of proliferative cells on the surface of a collagen gel. To explore other types of ECMs that can be used to build biomimetic scaffolds, we mixed Matrigel (protein concentration 8.7 mg/mL) and collagen (2 mg/mL) at different volumetric ratios and polymerized the resulting hydrogel at 37° C. for 1 h. The colonic epithelial cells were plated on the scaffolds and cultured under ENR-WB (see below for definition) for 5 days. The cells formed different morphologies (FIG. 8). The cells spread to form a 2D monolayer when the Matrigel composition was less than 25%, while the cells formed 3D spheroids when the Matrigel composition was higher than 50%. Our result show for the first time that 3D organoids can be formed on the top surface of Matrigel, without requiring the encapsulation of cells. One advantage is that all organoids are located on the same imaging plane for subsequent microscopic analysis.

Matrigel is very soft and its elastic modulus as determined by atomic force microscopy is as low as 450 Pa (Soofi, S. S. et al., *Journal of Structural Biology* 167, 216-219 (2009)). The collagen gel is much stiffer than Matrigel and it has a linear modulus of 200 KPa at 2 mg/mL concentration (Cummings, C. L. et al., *Biomaterials* 25, 3699-3706 (2004)).[2] The elastic modulus of small-intestine submucosa (a cell-free collagen derived from the small intestine by mechanical removal of the mucosal and smooth muscle layers) is around 132-549 KPa (Roeder, R. et al., *J. Biomed Mater Res.* 47, 65-70 (1999)). Therefore, collagen is better than Matrigel in terms of mimicking this biophysical property of the submucosa on which the epithelium resides. Our result suggest that biophysical property (e.g., stiffness) plays a role in determining the morphology of colonic epithelium indicating that it is necessary to finely adjust the biophysical properties of the scaffold.

EXAMPLE 4

Additional Evidence that 2D Monolayer on Biomimetic Scaffolds is Multipotent and can be Selectively Differentiated to Specialized Cells The in vivo colonic epithelium is composed of not only stem/progenitor cells, but also differentiated, specialized cells (enterocytes, goblet cells, enteroendocrine cells). The function of stem/progenitor cells is to provide the source for the renewal of short-lived specialized cells. The functions of specialized cells range from absorption (enterocytes), mucus secretion (goblet cells), and hormone production (enteroendocrine cells). It is thus highly desirable to generate specialized cells for in vitro functional study of colon epithelium as a mimic of the in vivo condition.

Figure 9:
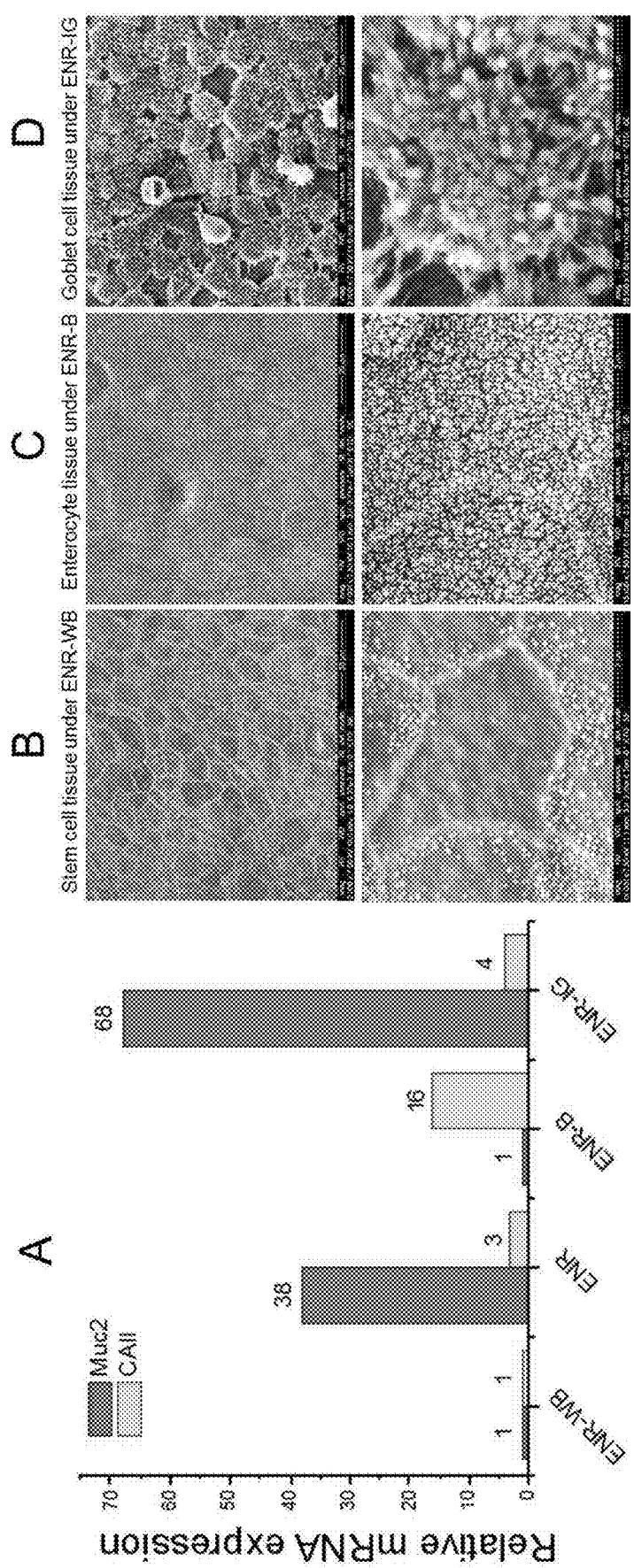
FIG. 9. Differentiation of a 2D monolayer to specialized cells. (A) Quantitative RT-PCR analysis of expression levels of mucin 2 (Muc2) and carbonic anhydrase II (CAII) for a 2D monolayer culture under four different conditions: ENR-WB, ENR, ENR-B, and ENR-IG. Relative gene expression is calculated with respect to 18S ribosomal RNA as housekeeping gene. (B)-(D) SEM images (top panel 2,000×, bottom panel 15,000×) of 2D monolayer cultured under ENR-WB, ENR-B and ENR-IG.

The stem/progenitor cells in the 2D monolayer were maintained by the activation of both Wnt and Notch signaling. We used Wnt-3A protein and R-spondin (Wnt signaling enhancer) to activate the Wnt signaling, and 0.5 mM sodium butyrate to activate Notch signaling. The medium used to maintain the proliferative stem/progenitor cells in the 2D monolayer is denoted as ENR-WB (E: epidermal growth factor, N: noggin, R: R-spondin: W: Wnt-3A, B: butyrate). The 2D monolayer under ENR-WB was inspected by scanning electron microscopy (SEM) (FIG. 9B). The cells in the 2D monolayer displayed a cobblestone-like morphology and arrangement, a characteristic of intestinal epithelium found in vivo. Some cells possessed a smooth surface, while other cells possessed low density microvilli at their apical surface.

To induce the differentiation towards the enterocyte lineage, we first cultured the 2D monolayer on collagen scaffold under ENR-WB for 4 days, and then treated the cells with ENR-B differentiation medium (removal of Wnt-3A protein) for 3 days. The 2D monolayer was inspected by SEM. Cells possessed high density of microvilli at their apical surface, a characteristic of absorptive enterocytes (FIG. 9C). Gene analysis (FIG. 9A) shows the enterocyte gene (CAII) is upregulated (16 times) in the ENR-B condition compared with the ENR-WB condition. Both SEM images and gene expression analysis show that the 2D monolayer cells were successfully differentiated to enterocyte cells under ENR-B.

To induce the differentiation towards goblet cell lineage, we first cultured the 2D monolayer on collagen scaffold under ENR-WB for 4 days, and then treated the cells with ENR-IG differentiation medium (I: IWP-2, G: gamma secretase inhibitor LY-411575) for 3 days. IWP-2 inhibited Wnt signaling, while LY-411575 inhibited Notch signaling. The 2D monolayer was inspected by SEM. The cells possessed vesicles on their apical surface to release mucus, a characteristic of mucus-secretive goblet cells (FIG. 9D). Gene analysis (FIG. 9A) shows the goblet cell gene (Muc2) is highly upregulated (68 times) in the ENR-IG condition compared with the ENR-WB condition. Both SEM images and gene expression analysis show that the 2D monolayer cells were successfully differentiated to goblet cells under the ENR-IG condition.

Based on the SEM images, we have presumptively concluded that the cells with smooth or low density of microvilli under the ENR-WB condition (FIG. 9B) are stem/progenitor cells. These cells are multipotent as they can be selectively differentiated to either enterocytes (ENR-B) or goblet cells (ENR-IG).

EXAMPLE 5

Figure 10:
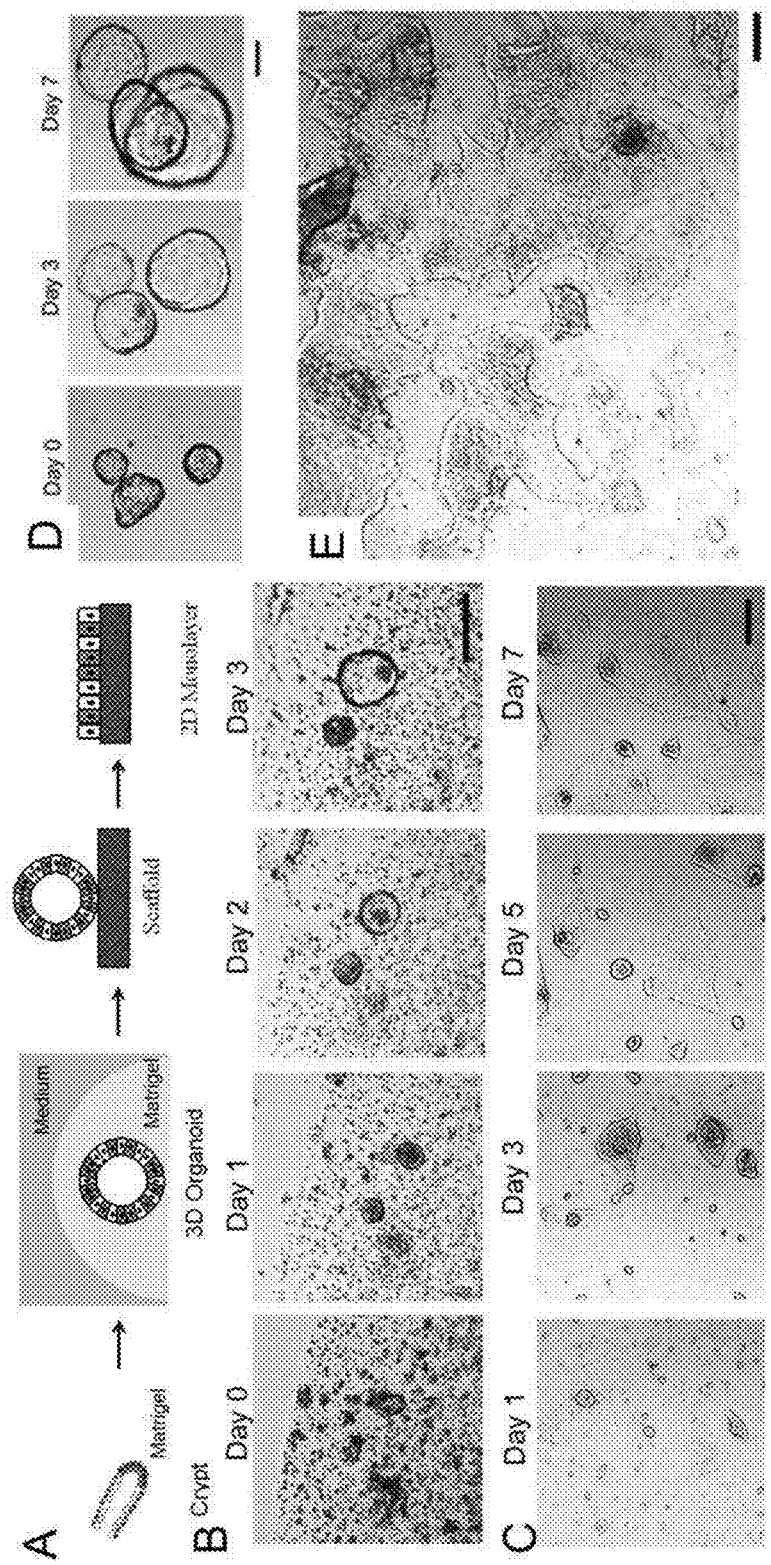
FIG. 10. Generating 2D monolayer models of human small intestine and colon. (A) Schematic. Proliferative cells are denoted with gray color, while differentiated cells are denoted with white color. (B) 3D organoid culture of human small intestine crypts. (C) Conversion of small intestine organoids to 2D monolayers. (D) 3D organoid culture of human colonic epithelial cells. (E) 2D monolayers generated from organoids at day 5 in culture. Scale bar=100 µm.

Human Small Intestinal and Colonic Epithelial Cells can be Cultured as 2D Monolayers We have extended the 2D monolayer culture technique from mouse to human small intestine and large intestine. To do so, the crypts were first isolated from human intestine and cultured in the 3D organoid model to expand the cells, including stem cells, progenitor cells and differentiated cells (FIG. 10). The organoids were then retrieved from Matrigel, and plated on the surface of a collagen hydrogel scaffold (1 mg/mL, rat tail collagen, type I). The 3D organoids were allowed to flatten on the scaffold and generated a proliferative, spreading 2D monolayer possessing an exposed luminal surface. The human cell culture medium was formulated prepared from a mixture of advanced DMEM/F12 medium, Wnt-3A-conditioned medium, R-spondin-2-conditioned medium, and Noggin-conditioned medium at a volumetric ratio of 3:1:1:1, and supplemented with EGF (50 ng/mL), N-acetyl cysteine (1.25 mM), GlutaMAX (1×), B27 (1×), Y27632 ROCK inhibitor (10 µM), HEPES (10 mM), A83-01 (500 ng/mL), prostaglandin E2 (10 nM), nicotinamide (10 mM), gastrin (10 nM), SB202190 (3 µM), penicillin (100 unit/mL), streptomycin (100 µg/mL), and gentamicin (5 µg/mL). The activity of Wnt-3A was determined to be 30 ng/mL by a TCF/LEF luciferase reporter stable HEK293 cell line (Signosis, #SL-0015) and calibrated with a recombinant Wnt-3a protein (R&D Systems, #1324-WN).

For human small intestine, biopsy tissue was obtained from a gastric bypass surgery. About 1,000 crypts were suspended in 1 mL medium. The suspension was centrifuge at 500 g for 5 min at 4° C. The pellet was suspended in 100 µL Matrigel, and 15 µL crypt/Matrigel suspension was plated in each well in a 24-well plate and incubated at 37° C. for 10 min to cure the Matrigel. 1 mL culture medium was added to each well. 3D organoids were observed to grow from crypts (FIG. 4B). The organoids were retrieved from Matrigel, and plated on the collagen hydrogel, which flattened and generated a proliferative, spreading 2D monolayer (FIG. 4C).

A similar result was obtained for human colonic epithelial cells. Human ascending colon was obtained from a donor (female, age 63). The colonic epithelial cells were first cultured as 3D organoids (FIG. 4D), and then converted to 2D monolayer (FIG. 4E). The data above demonstrate that human intestinal epithelial cells can be spread on the biomimetic scaffold to form a 2D monolayer with an open luminal surface.

EXAMPLE 6

Figure 11A:
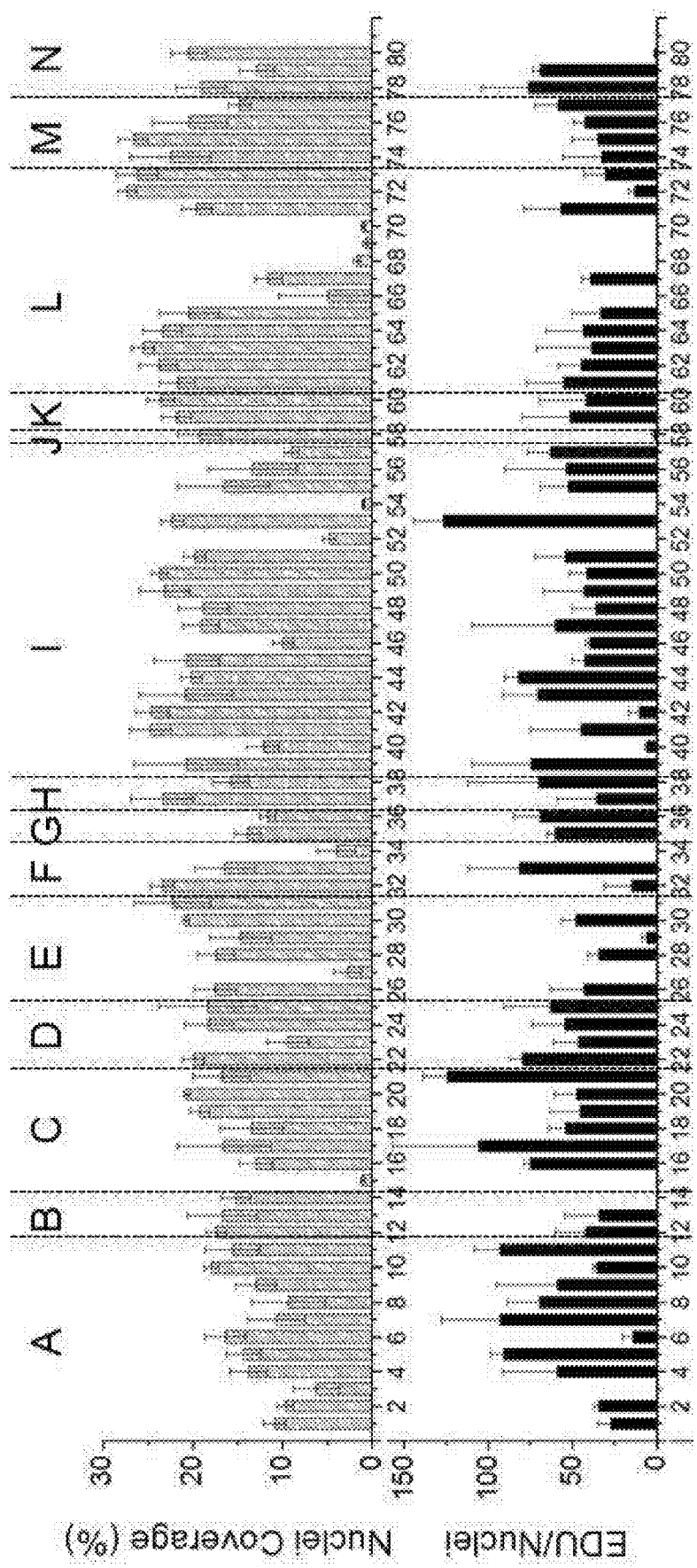
FIG. 11. The impact of dietary compounds and natural products on primary colonic epithelium. The percentage of the collagen Daiszein (aglycone of daidzen) surface area occupied by cells (Hoechst 33342-positive) and the normalized EDU (A), alkaline phosphatase and mucin2-positive areas (B) were plotted against the compound number. The EDU, alkaline phosphatase and Muc2 areas were normalized to the total cell area. Alphabetic headings refer to categories described in Table 1.
Figure 11B:
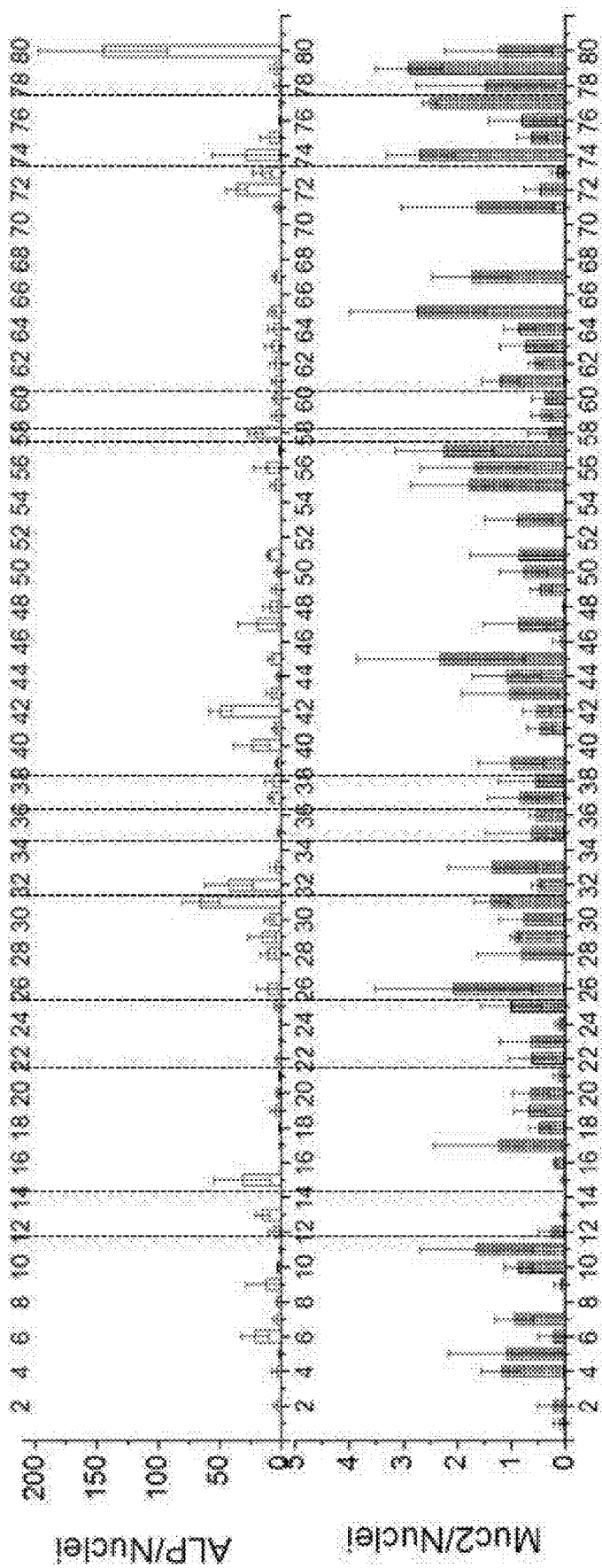

High-Throughput Screening of Dietary Metabolites and Natural Products Using Primary Intestinal Epithelium Strategies to screen the vast number of dietary and metabolite compounds for their impact on proliferation, differentiation and other cell behaviors in the intestine have become increasingly important. However, major challenges exist due to a lack of technologies capable of faithfully duplicating the actions of these compounds on normal, healthy colonic cells. To demonstrate the potential for the in vitro planar intestinal tissue platform as a screening tool, seventy-seven compounds (listed in Table 1) were screened for their ability to alter proliferation and differentiation of primary intestinal epithelial cells. These attributes are central to intestinal barrier function and repair in the face of repeated chemical, physical, immune and infectious insults. Additionally controlled proliferation and terminal differentiation are key to avoiding an oncogenic state. Metabolites or natural products minimizing intestinal-cell proliferation without cell death, enhancing cell proliferation, or directing cells into the differentiated lineages are of profound interest for health maintenance and as therapeutics. The compounds represented a range of chemical classes with diverse or unknown impact on primary intestinal cells including fatty acids, bile acids, flavenoids, phytoestrogens, phenols, terpenoids, nitrates, and others. 75,000 cells were cultured on the collagen hydrogel with ENR-W (but with 10 ng/mL Wnt-3A) for 24 h to enable cells to attach to the surface, followed by incubation with the dietary/natural compounds for 48 h. The cells were then analyzed sequentially for four attributes: nuclei (Hoechst 33342), S-phase or proliferating cells (EDU), enterocyte phenotype (high alkaline phosphatase), and goblet cell marker (Muc2) (FIGS. 11A-B). A number of compounds were growth suppressive in that both the number of nuclei and S-phase cells was significantly lower ($p<0.01$) than that of the control cells (cultured in ENR-W). These included many of the fatty acids, nitrates, terpenoids and curcuminoids, all which are known to either promote differentiation or exhibit cell toxicity. In particular, glucosinolates (#68, #69, #70), responsible for the bitterness of cabbage and brussel sprouts, are toxic when consumed at high concentrations and this may in part be due to their direct effects on intestinal cells. Staurosporine (#32) significantly increased the number of nuclei but decreased S-phase cells relative to that of the control suggesting initial proliferation followed by later apoptosis. A number of compounds did not greatly diminish cell number but suppressed proliferation, a feature that may enable them to diminish cancer risk. These included the most of the phenols assayed such as gallic acid (#28), ellagic acid (#29), and punicalagin (#31) but also compounds such as valproate (#6) and □-carotene (#58) all of which are recognized in the literature as inducing cell differentiation. Isorhamnetin (#21) found in Ginkgo biloba, increased cell numbers in S-phase which may be one source of this natural product's ability to mitigate intestinal damage in the face of toxins. Surprisingly, eucalyptol (#42) used in flavorings, fragrances, and cosmetics also minimized cell proliferation and pushed the cells towards the enterocyte lineage increasing alkaline phosphatase expression ($p=0.01$). Other compounds that directed cells towards the enterocyte lineage without cell number reduction were punicalagin (#31; $p=0.02$) an antioxidant found in pomegranates and phytol (#51; $p=0.002$) a nuclear-receptor ligand used in the fragrance industry. Molecules promoting enterocyte formation may exert some of their beneficial effects by enhancing intestinal barrier and/or absorptive function and thus may be worthy of additional investigation. A single compound, matairesinol (#77), significantly increased Muc2 or mucin expression ($p<0.01$). Matairesinol increases COX-2-derived prostaglandin E2 in Caco-2 cells and prostaglandin E2 has been characterized as inducing Goblet cell formation in the colon to increase mucous secretion. Screening primary colon epithelium directly links the matairesinol to increased mucous production and this may be through a prostaglandin E pathway.

TABLE 1

List of dietary compounds and natural products and their working concentration for study.

| # | Category 1 | Category 2 | Compound Name | Concentration for Study (mM) |
|---|---|---|---|---|
| 1 | (A) Fatty Acids | Short Chain Fatty Acids (SCFAs) | Acetate | 24 |
| 2 | | | Butyrate | 1 |
| 3 | | | Propionate | 6 |
| 4 | | | 3-Hydroxybutyrate | 5 |
| 5 | | | Formate | 10 |
| 6 | | | Valproate | 2 |
| 7 | | Medium Chain Fatty Acids | Capric Acid/Decanoic acid | 0.1 |
| 8 | | Long Chain Fatty Acids | Docosahexanoic Acid | 0.1 |
| 9 | | Other Acids | Nicotinic Acid | 5 |
| 10 | | | Succinic Acid | 2 |
| 11 | | | Pamoic Acid | 0.001 |
| 12 | (B) Secondary Bile Acids | | Deoxycholic Acid | 0.001 |
| 13 | | | Ursodeoxycholic Acid | 0.188 |
| 14 | | | Hyodeoxycholic Acid | 0.188 |
| 15 | (C) Flavenoids | | Luteolin | 0.25 |
| 16 | | | Tangeritin | 0.05 |
| 17 | | | Quercetin | 0.05 |
| 18 | | | Kaempferol | 0.06 |
| 19 | | | Myricetin | 0.04 |
| 20 | | | Fisetin | 0.01 |
| 21 | | | Isorhamnetin | 0.05 |
| 22 | (D) Phytoestrogens | | Daidzin | 0.02 |
| 23 | | | Genistin | 0.03 |
| 24 | | | Daiszein (aglycone of daidzen) | 0.05 |
| 25 | | | Genistein (aglycine of genistin) | 0.015 |
| 26 | (E) Phenols | | Carbolic Acid (Phenol) | 0.034 |
| 27 | | | Tannic Acid | 0.034 |
| 28 | | | Gallic Acid | 0.02 |
| 29 | | | Ellagic Acid | 0.06 |
| 30 | | | Chlorogenic Acid | 0.06 |

TABLE 1-continued

List of dietary compounds and natural products and their working concentration for study.

| # | Category 1 | Category 2 | Compound Name | Concentration for Study (mM) |
|---|---|---|---|---|
| 31 | | | Punicalagin | 0.01 |
| 32 | | (F) Stilbenes | Aglycones (Staurosporine) | 0.0003 |
| 33 | | | Pinosylvin | 0.001 |
| 34 | | | Resveratrol | 0.1 |
| 35 | | (G) Curcuminoids | Bisdemethoxycurcumin | 0.034 |
| 36 | | | Demethoxycurcumin | 0.034 |
| 37 | | (H) Chalconoids | Dihydrochalcone | 0.034 |
| 38 | | | Chlacone | 0.02 |
| 39 | | (I) Terpenoids | Isoprene | 5 |
| 40 | | | Isovaleric Acid | 10 |
| 41 | | | Geranyl Pyrophosphate | 0.015 |
| 42 | | | Eucalyptol | 1 |
| 43 | | | R-Limonene | 1 |
| 44 | | | Pinene | 0.3 |
| 45 | | | Farnesyl Pyrophosphate | 0.015 |
| 46 | | | Artemisinin | 0.1 |
| 47 | | | Bisabolol | 0.005 |
| 48 | | | Geranylgeranyl Pyrophosphate | 0.005 |
| 49 | | | Retinol | 0.001 |
| 50 | | | Retinal | 0.000001 |
| 51 | | | Phytol | 0.2 |
| 52 | | | Taxol (Paclitaxel) | 0.02 |
| 53 | | | Forskolin | 0.005 |
| 54 | | | Aphidicolin | 0.06 |
| 55 | | | Salvinorin | 0.001 |
| 56 | | | Squalene | 0.05 |
| 57 | | | Lanosterol | 0.04 |
| 58 | | (J) Carotenoids | β-carotene | 5 |
| 59 | | (K) Phytosterols | β-Sitosterol | 0.13 |
| 60 | | | Campesterol | 0.006 |
| 61 | (L) | Nitrosamines | N-nitrosonornicotine | 0.001 |
| 62 | Nitrates | | 4-(methylnitrosamino)-1-(3-pyridyl)-1-butanone | 0.01 |
| 63 | | | N-nitrosodimethylamine | 0.05 |
| 64 | | | N-nitrodiethylamine | 2 |
| 65 | | | N-nitrosoanabasine | 0.989 |
| 66 | | Nitrosoguanidine | N-methyl-N-nitroso-p-toluenesulfonamide | 0.989 |
| 67 | | Glucosinolates | Sinigrin | 0.989 |
| 68 | | | Glucotropaeolin isothiocyanate | 6 |
| 69 | | | Gluconasturtiin | 0.1 |
| 70 | | | Glucoraphanin | 1 |
| 71 | | Indoles | Indole | 0.675 |
| 72 | | | Indole-3-butyric acid | 0.058 |
| 73 | | | 3-Methylindole | 0.000005 |
| 74 | | (M) Plant Lignins | Enterodiol | 0.01 |
| 75 | | | Enterolactone | 0.01 |
| 76 | | | Secoisolariciresinol | 0.1 |
| 77 | | | Matairesinol | 0.05 |
| 78 | (N) | ENR-W medium | Containing 10 ng/mL Wnt-3A | |
| 79 | Control | ENR-W + DMSO | Containing 1/1000 DMSO | |
| 80 | | ENR | Differentiation medium | |
| 81 | | No cells | Collagen hydrogel | |

REFERENCES

1. N. Barker, M. van de Wetering and H. Clevers, *Genes & Development,* 2008, 22, 1856-1864.
2. E. Fuchs and T. Chen, *Embo Reports,* 2013, 14, 39-48.
3. M. Brittan and N. A. Wright, *Gut,* 2004, 53, 899-910.
4. C. Kosinski, V. S. W. Li, A. S. Y. Chan, J Zhang, C. Ho, W. Y. Tsui, T. L. Chan, R. C. Mifflin, D. W. Powell, S. T. Yuen, S. Y. Leung and X. Chen, *Proc. Natl. Acad. Sci. U.S.A.,* 2007, 104, 15418-15423.
5. T. H. Yen and N. A. Wright, *Stem Cell Rev.,* 2006, 2, 203-212.
6. G. L. Eastwood and J. S. Trier, *Gastroenterology,* 1973, 64, 375-382.
7. H. Autrup, L. A. Barrett, F. E. Jackson, M. L. Jesudason, G. Stoner, P. Phelps, B. F. Trump and C. C. Harris, *Gastroenterology,* 1978, 74, 1248-1257.
8. C. Booth, S. Patel, G. R. Bennion and C. S. Potten, *Epithelial Cell Biol.,* 1995, 4, 76-86.
9. R. H. Whitehead, A. Brown and P. S. Bhathal, *In Vitro Cellular & Developmental Biology,* 1987, 23, 436-442.
10. J. B. Seidelin, T. Horn and O. H. Nielsen, *Am. J. Physiol.-Gastroint. Liver Physiol.,* 2003, 285, G1122-G1128.
11. A. Quaroni, *Gastroenterology,* 1989, 96, 535-536.

12. T. Sato, R. G. Vries, H. J. Snippert, M. van de Wetering, N. Barker, D. E. Stange, J. H. van Es, A. Abo, P. Kujala, P. J. Peters and H. Clevers, *Nature,* 2009, 459, 262-U147.
13. T. Sato, J. H. van Es, H. J. Snippert, D. E. Stange, R. G. Vries, M. van den Born, N. Barker, N. F. Shroyer, M. van de Wetering and H. Clevers, *Nature,* 2010.
14. T. Sato, D. E. Stange, M. Ferrante, R. G. Vries, J. H. Van Es, S. Van den Brink, W. J. Van Houdt, A. Pronk, J. Van Gorp, P. D. Siersema and H. Clevers, *Gastroenterology,* 2011, 141, 1762-1772.
15. P. Jung, T. Sato, A. Merlos-Suarez, F. M. Barriga, M. Iglesias, D. Rossell, H. Auer, M. Gallardo, M. A. Blasco, E. Sancho, H. Clevers and E. Battle, *Nature Medicine,* 2011, 17, 1225-1227.
16. S. R. Yui, T. Nakamura, T. Sato, Y. Nemoto, T. Mizutani, X. Zheng, S. Ichinose, T. Nagaishi, R. Okamoto, K. Tsuchiya, H. Clevers and M. Watanabe, *Nature Medicine,* 2012, 18, 618-623.
17. M. Stelzner, M. Helmrath, J. C. Y. Dunn, S. J. Henning, C. W. Houchen, C. Kuo, J. Lynch, L. H. Li, S. T. Magness, M. G. Martin, M. H. Wong, J. Yu and N. I. H. I. S. C. Consortiu, *Am. J. Physiol.-Gastroint. Liver Physiol.,* 2012, 302, G1359-G1363.
18. Y. L. Wang, A. A. Ahmad, C. E. Sims, S. T. Magness and N. L. Allbritton, *Lab Chip,* 2014, 14, 1622-1631.
19. C. Moon, K. L. VanDussen, H. Miyoshi and T. S. Stappenbeck, *Mucosal Immunol,* 2014, 7, 818-828.
20. K. L. VanDussen, J. M. Marinshaw, N. Shaikh, H. Miyoshi, C. Moon, P. I. Tarr, M. A. Ciorba and T. S. Stappenbeck, *Gut,* 2014, doi:10.1136/gutjnl-2013-306651
21. D. R. Donohoe, N. Garge, X. X. Zhang, W. Sun, T. M. O'Connell, M. K. Bunger and S. J. Bultman, *Cell Metabolism,* 2011, 13, 517-526.
22. J. R. Davie, *Journal of Nutrition,* 2003, 133, 2485S-2493S.
23. M. A. Cayo, A. K. Cayo, S. M. Jarjour and H. Chen, *American Journal of Translational Research,* 2009, 1, 178-183.
24. X. L. Yin, H. F. Farin, J. H. van Es, H. Clevers, R. Langer and J. M. Karp, *Nature Methods,* 2014, 11, 106-+.
25. E. J. Formeister, A. L. Sionas, D. K. Lorance, C. L. Barkley, G. H. Lee and S. T. Magness, *Am. J. Physiol.-Gastroint. Liver Physiol.,* 2009, 296, G1108-G1118.
26. H. J. Kim, D. Huh, G. Hamilton and D. E. Ingber, *Lab Chip,* 2012, 12, 2165-2174.
27. Q. Ramadan, H. Jafarpoorchekab, C. B. Huang, P. Silacci, S. Carrara, G. Koklu, J. Ghaye, J. Ramsden, C. Ruffert, G. Vergeres and M. A. M. Gijs, *Lab Chip,* 2013, 13, 196-203.
28. J. H. Sung, J. J. Yu, D. Luo, M. L. Shuler and J. C. March, *Lab Chip,* 2011, 11, 389-392.
29. J. H. Sung, M. B. Esch, J. M. Prot, C. J. Long, A. Smith, J. J. Hickman and M. L. Shuler, *Lab Chip,* 2013, 13, 1201-1212.

The foregoing is illustrative of the present invention, and is not to be construed as limiting thereof. The invention is defined by the following claims, with equivalents of the claims to be included therein.

That which is claimed is:

1. A method of making a live cell construct, comprising:
   (a) providing a non-cellular support having a top surface and a bottom surface, wherein the non-cellular support, comprises an elastic modulus of less than about 550 KPa, wherein the non-cellular support comprises a hydrogel formed from a natural or synthetic polymer,
   (b) contacting live primary undifferentiated gastrointestinal epithelial cells to said non-cellular support, and then
   (c) propagating a self-renewing monolayer of live primary gastrointestinal epithelial cells on said top surface, wherein the live primary gastrointestinal epithelial cells comprise at least some undifferentiated cells, wherein a number of live primary gastrointestinal epithelial cells, including undifferentiated cells, in the self-renewing monolayer is maintained or increased for at least 24 hours.

2. The method of claim 1, wherein said monolayer comprises primary differentiated cells in combination with said primary undifferentiated cells.

3. The method of claim 1, wherein said primary gastrointestinal epithelial cells are selected from the group consisting of mammalian, avian, reptilian, amphibian, and insect cells.

4. The method of claim 1, wherein said primary gastrointestinal epithelial cells are primary human gastrointestinal epithelial cells.

5. The method of claim 1, wherein said primary gastrointestinal epithelial cells are selected from the group consisting of colon, small intestine, stomach, esophagus, tongue, nasopharynx, oropharynx, laryngeopharynx, and pancreatic epithelial cells.

6. The method of claim 1, further comprising the step of:
   (d) contacting a culture media to said self-renewing monolayer of live primary gastrointestinal cells, which culture media sustains said self-renewing monolayer of live primary gastrointestinal cells.

7. The method of claim 6, wherein said culture media comprises a short-chain fatty acid, Wnt-3A, R-spondin, noggin and epidermal growth factor (EGF).

8. The method of claim 1, wherein said support comprises collagen, gelatin, laminin, elastin, fibronectin, heparin sulfate, chondroitin sulfate, keratin sulfate, hyaluronic acid, gelatinous protein mixture secreted by Engelbreth-Holm-Swarm mouse sarcoma cells, and combinations thereof; and/or said support comprises a hydrogel formed from a natural or synthetic polymer.

9. The method of claim 1, wherein the support is porous and/or the support bottom surface is on a porous carrier, a mesh, an inorganic grid, a hydrogel, or a combination thereof.

10. The method of claim 1, said top surface having a plurality of wells formed therein, each of said wells having a top opening, side walls and a floor; said self-renewing gastrointestinal epithelial cell monolayer extending onto said well side walls and floors, with the well top openings remaining open, to form open lumens lined with cells in said wells.

11. A live cell construct, comprising:
   (a) a non-cellular support having a top surface and a bottom surface, wherein the non-cellular support comprises an elastic modulus of less than about 550 KPa, wherein the non-cellular support comprises a hydrogel formed from a natural or synthetic polymer;
   (b) a self-renewing monolayer of live primary gastrointestinal epithelial cells formed on said top surface, wherein the live primary gastrointestinal epithelial cells comprise at least some undifferentiated cells, wherein a number of live primary gastrointestinal epithelial cells, including undifferentiated cells, in the self-renewing monolayer is maintained or increased for at least 24 hours.

12. The construct of claim 11, wherein said live primary gastrointestinal epithelial cells in said monolayer comprise differentiated cells in combination with said undifferentiated cells.

13. The construct of claim 11, wherein said primary gastrointestinal epithelial cells are selected from the group consisting of mammalian, avian, reptilian, amphibian, and insect cells.

14. The construct of claim 11, wherein said primary gastrointestinal epithelial cells are primary human gastrointestinal epithelial cells.

15. The construct of claim 11, wherein said primary gastrointestinal epithelial cells are selected from the group consisting of colon, small intestine, stomach, esophagus, tongue, nasopharynx, oropharynx, laryngeopharynx, and pancreatic epithelial cells.

16. The construct of claim 11, further comprising:
(c) a culture medium contacting said self-renewing monolayer of live primary gastrointestinal epithelial cells, which culture medium sustains said self-renewing monolayer of live primary gastrointestinal epithelial cells.

17. The construct of claim 16, wherein said culture medium comprises a short-chain fatty acid, Wnt-3A, R-spondin, noggin and epidermal growth factor (EGF).

18. The construct of claim 11, wherein said support comprises collagen, gelatin, laminin, elastin, fibronectin, heparan sulfate, chondroitin sulfate, keratan sulfate, hyaluronic acid, gelatinous protein mixture secreted by Engelbreth-Holm-Swarm mouse sarcoma cells, and combinations thereof; and/or said support comprises a hydrogel formed from a natural or synthetic polymer.

19. The construct of claim 11, wherein the support is porous and/or the support bottom surface is on a porous carrier, an inorganic grid, a hydrogel, or a combination thereof.

20. The construct of claim 11, said top surface having a plurality of wells formed therein, each of said wells having a top opening, side walls and a floor;
said self-renewing gastrointestinal epithelial cell monolayer extending onto said well side walls and floors, with said well top openings remaining uncovered, to form open cell lumens in said wells.

21. The construct of claim 20, wherein said wells are from about 100 to about 1000 microns deep, and/or said wells are from about 10 to about 200 microns wide; and/or at least about 10 to about 100 of said wells are formed in said top surface.

22. The construct of claim 20, wherein:
said live primary cells in said self-renewing monolayer comprise both differentiated cells and undifferentiated cells in combination;
said differentiated cells and said undifferentiated cells are positioned in said monolayer in a gradient with a greater concentration of differentiated cells on one end of the gradient; and a greater concentration of undifferentiated cells on the other end of said gradient;
said gradient oriented with or along said well side walls.

23. A method of screening a test compound or test microbe for a toxicological, physiological, or carcinogenic effect, comprising:
(a) providing a construct according to claim 11,
(b) contacting a test compound or test microbe to said construct; and then
(c) detecting a toxicological, physiological, or carcinogenic effect of said test compound or test microbe on the cells of said construct.

24. The method of claim 23, wherein said test compound is selected from the group consisting of aromatic organic compounds, aliphatic organic compounds, and mixed aromatic and aliphatic organic compounds and/or the microbe is selected from the group consisting of gram negative bacteria, gram positive bacteria, yeast, and molds.

* * * * *